US008846366B2

(12) United States Patent
Gaisberger et al.

(10) Patent No.: US 8,846,366 B2
(45) Date of Patent: Sep. 30, 2014

(54) R-HYDROXYNITRILE LYASE (R-HNL) RANDOM VARIANTS AND THEIR USE FOR PREPARING OPTICALLY PURE, STERICALLY HINDERED CYANOHYDRINS

(75) Inventors: Richard Gaisberger, Velden/Worthersee (AT); Anton Glieder, Gleisdorf (AT); Zhibin Liu, Jurrong Island (SG); Beate Pscheidt, Hart-Purgstall (AT)

(73) Assignee: DSM IP Assets BV, Heerlen (NL)

( * ) Notice: Subject to any disclaimer, the term of this patent is extended or adjusted under 35 U.S.C. 154(b) by 941 days.

(21) Appl. No.: 12/519,095

(22) PCT Filed: Dec. 11, 2007

(86) PCT No.: PCT/EP2007/063692
§ 371 (c)(1),
(2), (4) Date: Feb. 23, 2010

(87) PCT Pub. No.: WO2008/071695
PCT Pub. Date: Jun. 19, 2008

(65) Prior Publication Data
US 2010/0143986 A1 Jun. 10, 2010

(30) Foreign Application Priority Data

Dec. 14, 2006 (AT) .............................. A 2064/2006
Aug. 23, 2007 (EP) .................................... 07016544

(51) Int. Cl.
| | |
|---|---|
| C12P 13/00 | (2006.01) |
| C07K 14/00 | (2006.01) |
| C12N 9/88 | (2006.01) |
| C12P 41/00 | (2006.01) |

(52) U.S. Cl.
CPC ................. *C12N 9/88* (2013.01); *C12P 13/004* (2013.01); *C12P 41/001* (2013.01)
USPC ............................ 435/232; 435/128; 530/350

(58) Field of Classification Search
USPC ............... 435/232, 440, 69.1, 320.1; 530/350
See application file for complete search history.

(56) References Cited

U.S. PATENT DOCUMENTS

| | | | |
|---|---|---|---|
| 4,859,784 A | 8/1989 | Effenberger et al. | |
| 5,008,192 A | 4/1991 | Neidermeyer et al. | |
| 5,795,747 A | 8/1998 | Henco et al. | |
| 6,046,042 A | 4/2000 | Hasslacher et al. | |
| 6,225,095 B1 | 5/2001 | Pöchlauer et al. | |
| 6,337,196 B1 | 1/2002 | Kirchner et al. | |
| 6,717,006 B1 | 4/2004 | Pöchlauer et al. | |
| 7,202,075 B2 | 4/2007 | Schwab et al. | |
| 8,030,053 B2 * | 10/2011 | Asano et al. | 435/252.3 |
| 2003/0119099 A1 | 6/2003 | Schwab et al. | |
| 2006/0105434 A1 | 5/2006 | Skranc et al. | |

FOREIGN PATENT DOCUMENTS

| | | |
|---|---|---|
| EP | 0 276 375 B1 | 5/1992 |
| EP | 0 547 655 A1 | 6/1993 |
| EP | 0 326 063 B1 | 9/1994 |
| EP | 0 528 256 B1 | 9/1996 |
| EP | 0 951 561 B1 | 8/2001 |
| EP | 1 238 094 B1 | 2/2004 |
| EP | 0 927 766 B1 | 6/2006 |
| EP | 1 566 441 B1 | 2/2009 |
| WO | WO 92/18645 A1 | 10/1992 |
| WO | WO 97/03204 A2 | 1/1997 |
| WO | WO 2006/041226 * | 4/2006 |
| WO | WO2006 076965 | 7/2006 |

OTHER PUBLICATIONS

Branden et al., Introduction to Protein Structure, Garland Publishing Inc., New York, p. 247, 1991.*
Seffernick et al. , J. Bacteriol. 183(8):2405-2410, 2001.*
Witkowski et al., Biochemistry 38:11643-11650, 1999.*
Glieder et al., Angew. Chem. Int. Ed. 42:4815-4818, 2003.*
Gaisberger et al., Counteracting expression deficiencies by anticipating posttranslational modification of PaHNL5-L1Q-A111G by genetic engineering, Journal of Biotechnology, 129 (2007) 30-38.
Weis et al., Serine scanning—A tool to prove the consequences of N-glycosylation of proteins, Journal of Biotechnology, 129 (2007) 50-61.
Abécassis, V. et al., "High Efficiency Family Shuffling Based on Multi-Step PCR and in vivo DNA Recombination in Yeast: Statistical and Functional Analysis of a Combinatorial Library Between Human Cytochrome P450 1A1 and 1A2," Nucleic Acids Research, 2000, 28 (20), e88, 10 pages.
Arnold, F. "Design by Directed Evolution," Accounts of Chemical Research, 1998, 31 (3), 125-131.
Bornscheuer, U., "High Throughput-Screening Systems for Hydrolases," Engineering in Life Sciences, 2004, 4 (6), 539-542.
Clouthier, C. et al., "Designing New Baeyer-Villiger Monooxygenases Using Restricted CASTing," Journal of Organic Chemistry, 2006, 71, 8431-8437.
Coco, W. et al., "DNA Shuffling Method for Generating Highly Recombined Genes and Evolved Enzymes," Nature Biotechnology, 2001, 19, 354-359.
Desantis, G. et al., "Creation of a Productive, Highly Enantioselective Nitrilase through Gene Site Saturation Mutagenesis (GSSM)," Journal of the American Chemical Society, 2003, 125, 11476-11477.
Doderer, K. et al., "Spectrophotometric Assay for Epoxide Hydrolase Activity Toward Any Epoxide," Analytical Biochemistry, 2003, 321, 131-134.
Gaisberger, R. et al., "Counteracting Expression Deficiencies by Anticipating Posttranslational Modification of PaHNL5-L1Q-A111G by Genetic Engineering," Journal of Biotechnology, 2007, 129 (1), 30-38, published online Dec. 9, 2006 (Applicants have not confirmed that the online publication is identical to the journal publication).

(Continued)

*Primary Examiner* — Delia Ramirez
(74) *Attorney, Agent, or Firm* — Hoxie & Associates LLC

(57) ABSTRACT

The invention relates to R-hydroxynitrile lyases with improved substrate acceptance, increased activity and increased selectivity, obtainable by introducing random mutations with the aid of random mutagenesis and/or saturation mutagenesis techniques, identifying by means of screening or selection and, where appropriate, subsequently combining advantageous mutations, and to the use thereof.

18 Claims, 7 Drawing Sheets

(56) References Cited

OTHER PUBLICATIONS

Goddard, J. et al., "Recent Advances in Enzyme Assays," Trends in Biotechnology, 2004, 22 (7), 363-370.

Heijne, G. et al., "Species-Specific Variation in Signal Peptide Design," Federation of European Biochemical Societies (FEBS Letters), 1989, 244 (2), 439-446.

Inan, M. et al., "Enhancement of Protein Secretion in *Pichia pastoris* by Overexpression of Protein Disulfide Isomerase," Biotechnology and Bioengineering, 2006, 93 (4), 771-778.

International Preliminary Report on Patentability for International Application No. PCT/EP2007/063692 date of issuance of the report Jun. 16, 2009, 6 pages.

Koizumi, H. et al., "High-Performance Liquid Chromatography of Aliphatic Aldehydes by Means of Post-Column Extraction with Fluorometric Detection," Journal of Chromatography, 1988, 457, 299-307.

Konarzycka-Bessler, M. et al., "A High Throughput-Screening Method for Determining the Synthetic Activity of Hydrolases," Angewandte Chemie International Edition, 2003, 42 (12), 1418-1420.

Kragl, U. et al., "Engineering Aspects of Enzyme Engineering, Continuous Asymmetric C—C Bond Formation in an Enzyme-Membrane-Reactor," Annals of the New York Academy of Sciences, 1990, 613 (1), 167-175.

Lutz, S., et al., "Rapid Generation of Incremental Truncation Libraries for Protein Engineering Using α-Phosphothioate Nucleotides," Nucleic Acids Research, 2001, 29 (4), e16, 7 pages.

Lutz, S. et al., "Creating Multiple-Crossover DNA Libraries Independent of Sequence Identity," Proceedings of the National Academy of Sciences, 2001, 98 (20), 11248-11253.

Ostermeier, M. et al., "Incremental Truncation as a Strategy in the Engineering of Novel Biocatalysts," Bioorganic and Medicinal Chemistry, 1999, 7, 2139-2144.

Ostermeier, M. et al., "A Combinatorial Approach to Hybrid Enzymes Independent of DNA Homology," Nature Biotechnology, 1999, 17, 1205-1209.

Persson, M. et al., "Effects of Solvent, Water Activity and Temperature on Lipase and Hydroxynitrile Lyase Enantioselectivity," Enzyme and Microbial Technology, 2002, 30, 916-923.

Raemaekers, R. et al., "Functional Phytohemagglutinin (PHA) and *Galanthus nivalis* Agglutinin (GNA) Expressed in *Pichia pastoris*, Correct N-terminal Processing and Secretion of Heterologous Proteins Expressed Using the PHA-E Signal Peptide," European Journal of Biochemistry, 1999, 265, 394-403.

Reetz, M. et al., "A Method for High-Throughput Screening of Enantioselective Catalysts," Angewandte Chemie International Edition, 1999, 38 (12), 1758-1761.

Reetz, M. et al., "A Practical NMR-Based High-Throughput Assay for Screening Enantioselective Catalysts and Biocatalysts," Advanced Synthesis and Catalysis, 2002, 344 (9), 1008-1016.

Sieber, V. et al., "Libraries of Hybrid Proteins from Distantly Related Sequences," Nature Biotechnology, 2001, 19, 456-460.

Stemmer, W., "Rapid Evolution of a Protein in vitro by DNA Shuffling," Nature, 1994, 370, 389-391.

Tielmann, P. et al., "A Practical High-Throughput Screening System for Enantioselectivity by Using FTIR Spectroscopy," Chemistry—A European Journal, 2003, 9, 3882-3887.

Weis, R. et al., "Serine Scanning—A Tool to Prove the Consequences of *N*-Glycosylation of Proteins," Journal of Biotechnology, 2007, 129 (1), 50-61, published online Dec. 9, 2006 (Applicants have not confirmed that the online publication is identical to the journal publication).

Weis, R. et al., "Biocatalytic Conversion of Unnatural Substrates by Recombinant Almond *R*-HNL Isoenzyme 5," Journal of Molecular Catalysis B: Enzymatic, 2004, 29, 211-218.

Wong, T. et al., "Sequence Saturation Mutagenesis (SeSaM): A Novel Method for Directed Evolution," Nucleic Acids Research, 2004, 32 (3), e26, DOI:10.1093/nar/gnh028, 8 pages.

Wong, T. et al., "Sequence Saturation Mutagenesis with Tunable Mutation Frequencies," Analytical Biochemistry, 2005, 341, 187-189.

Xiong, A. et al., "Isolation, Characterization, and Molecular Cloning of the cDNA Encoding a Novel Phytase from *Aspergillus niger* 113 and High Expression in *Pichia pastoris*," Journal of Biochemistry and Molecular Biology, 2004, 37 (3), 282-291.

Xiong, A. et al., "High Level Expression of a Synthetic Gene Encoding *Peniophora lycii* Phytase in Methylotrophic Yeast *Pichia pastoris*," Applied Microbiology and Biotechnology, 2006, 72, 1039-1047.

Zhang, W. et al., "Enhanced Secretion of Heterologous Proteins in *Pichia pastoris* Following Overexpression of *Saccharomyces cerevisiae* Chaperone Proteins," Biotechnology Progress, 2006, 22, 1090-1095.

Zhao, H. et al., "Molecular Evolution by Staggered Extension Process (StEP) in vitro Recombination," Nature Biotechnology, 1998, 16, 258-261.

* cited by examiner

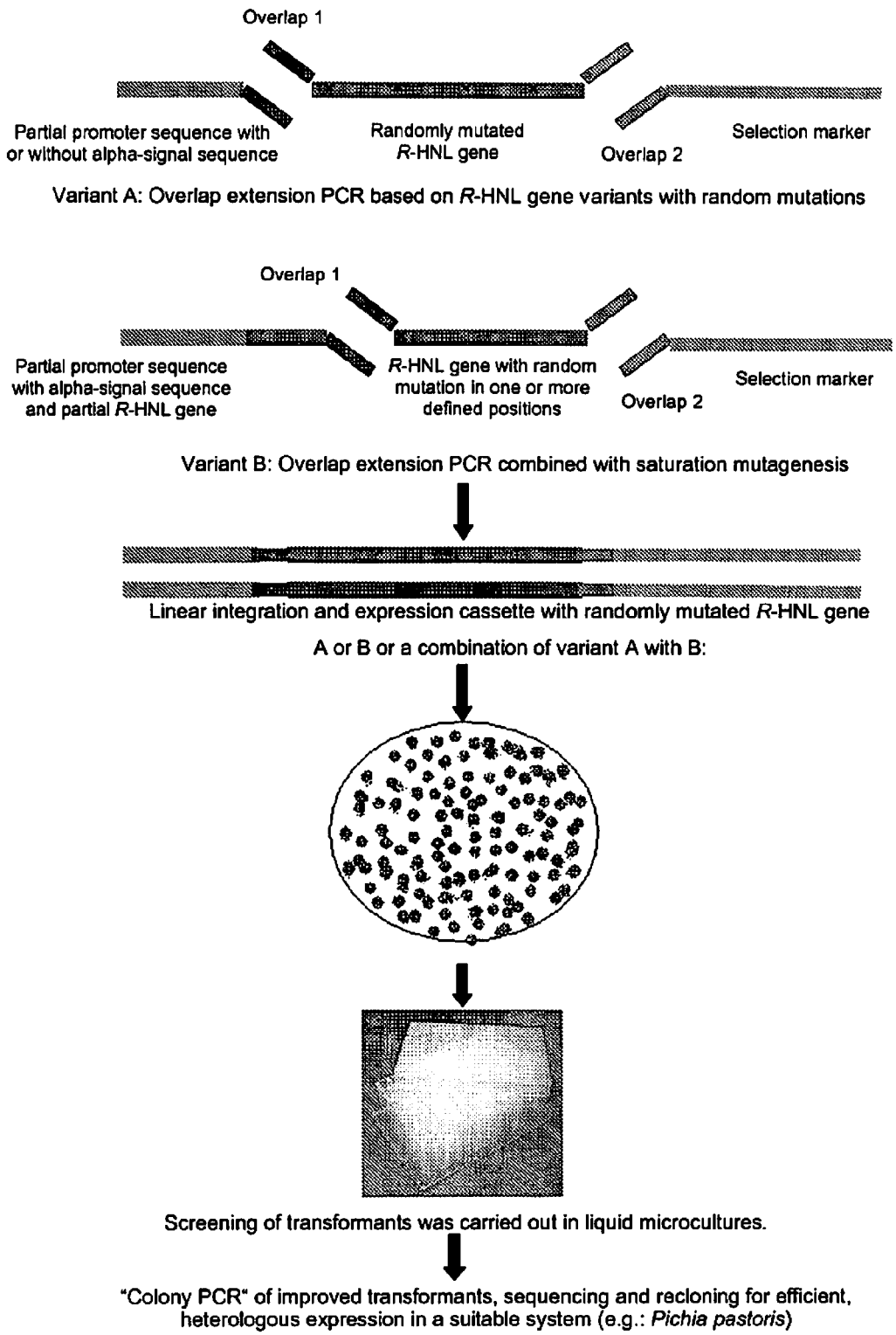
Figure 1: Preparation of R-HNL libraries and subsequent culturing of the new variants in liquid microcultures

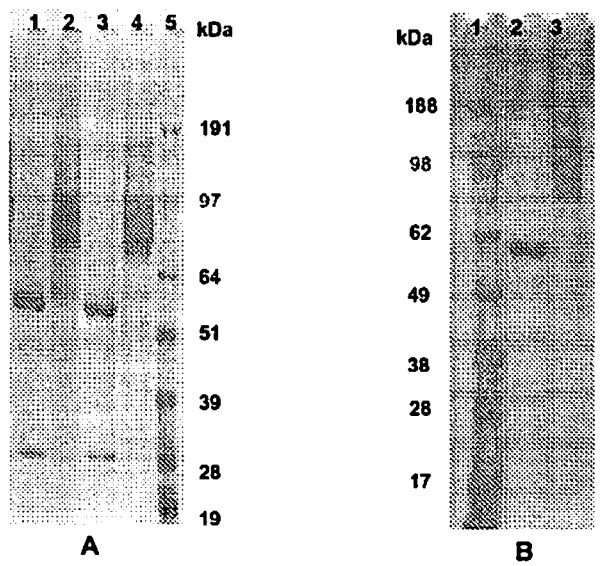
A) Protein gel NuPAGE 4-12% to gel with NuPAGE MOPS buffer:
1 - PaHNL5-V317G deglycosylated;
2 - PaHNL5-V317G native;
3 - PaHNL5-V317A deglycosylated;
4 - PaHNL5-V317A native;
5 - Standard SeeBlue® Plus2
B) Protein gel NuPAGE 4-12% to gel with NuPAGE MES buffer:
1 - Standard SeeBlue® Plus2
2 - PaHNL5αL1Q deglycosylated;
3 - PaHNL5αL1Q native;
Figure 2: Native and EndoH-deglycosylated protein samples of PaHNL5αL1Q (=WT), V317G and V317A

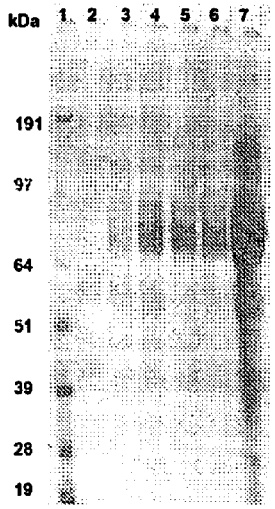

Figure 3: Native V317A protein samples taken at various points in time of the 5 l fermentation (protein gel NuPAGE 4-12% to gel with NuPAGE MOPS buffer)
1 - Standard SeeBlue® Plus2
2 - V317A_5 l fermentation, start of methanol addition
3 - V317A_5 l fermentation, 10 h 40 min after start of methanol addition
4 - V317A_5 l fermentation, 35 h 15 min after start of methanol addition
5 - V317A_5 l fermentation, 59 h 10 min after start of methanol addition
6 - V317A_5 l fermentation, 67 h 50 min after start of methanol addition
7 - V317A_5 l fermentation, concentrated enzyme preparation

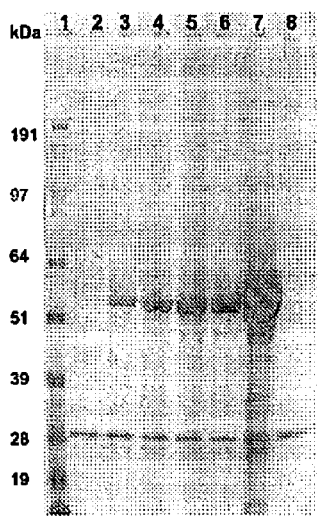

Figure 4: Deglycosylated V317A protein samples taken at various points in time of the 5 l fermentation (protein gel NuPAGE 4-12% to gel with NuPAGE MOPS buffer)
1 - Standard SeeBlue® Plus2
2 - V317A_5 l fermentation, start of methanol addition
3 - V317A_5 l fermentation, 10 h 40 min after start of methanol addition
4 - V317A_5 l fermentation, 35 h 15 min after start of methanol addition
5 - V317A_5 l fermentation, 59 h 10 min after start of methanol addition
6 - V317A_5 l fermentation, 67 h 50 min after start of methanol addition
7 - V317A_5 l fermentation, concentrated enzyme preparation
8 - V317A_5 l fermentation, ultrafiltration flowthrough

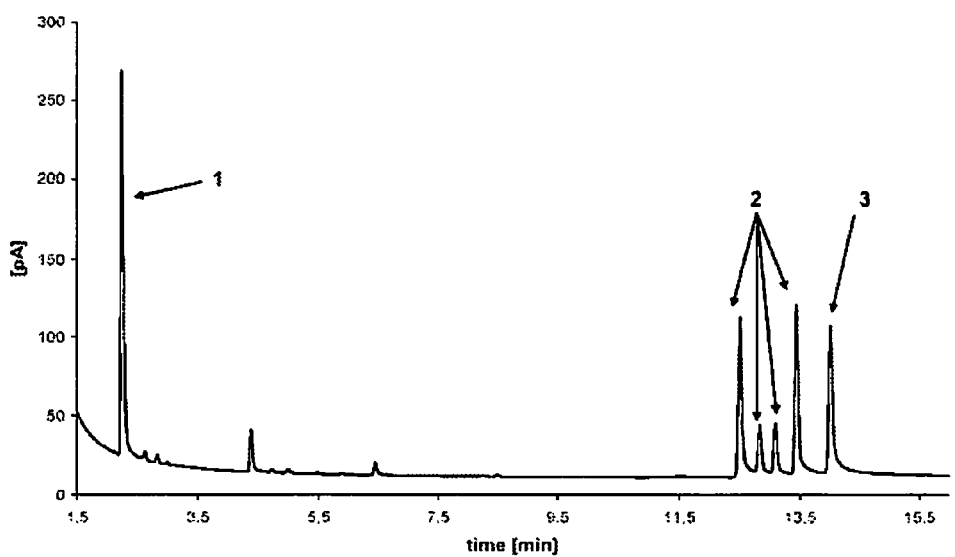
Figure 5: Chromatogram of a mixture of hydroxypivalaldehyde monomer (1), dimer (2) and Tishchenko ester (3) after acetylation and fractionation through a chiral column (CP-Chirasil-DEX CB)

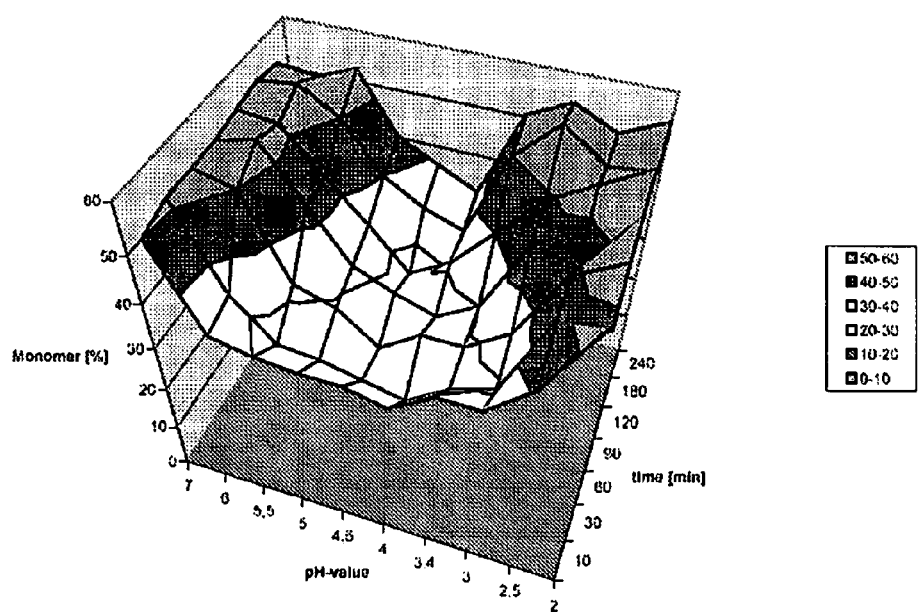
Figure 6: Proportion of hydroxypivalaldehyde monomer after different incubation times in aqueous buffer solutions at different pH values

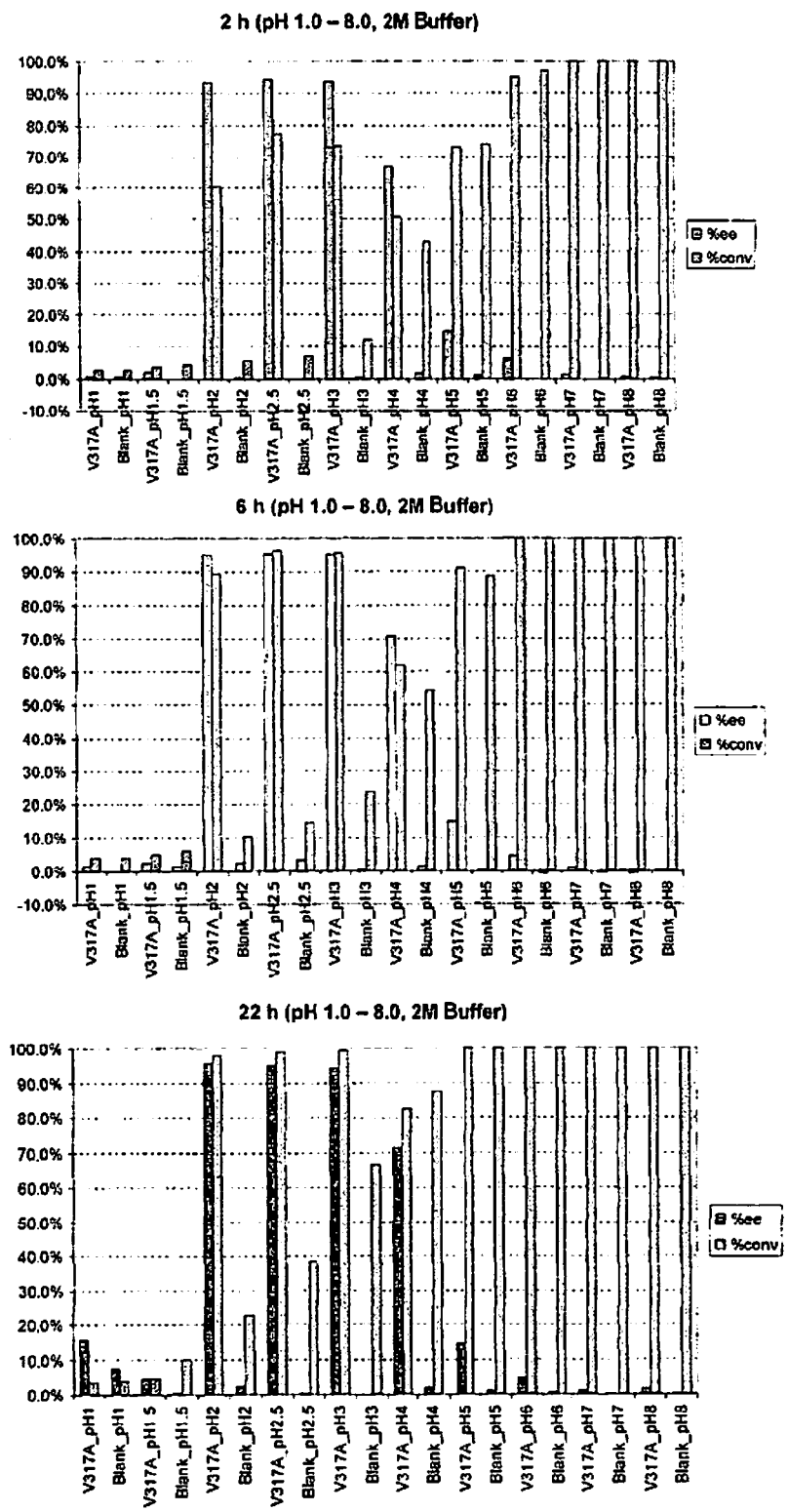
Figure 7: Conversion and enantiomeric excess for V317A at various pH values after 2h, 6h and 22h. A 2M potassium phosphate buffer was used.

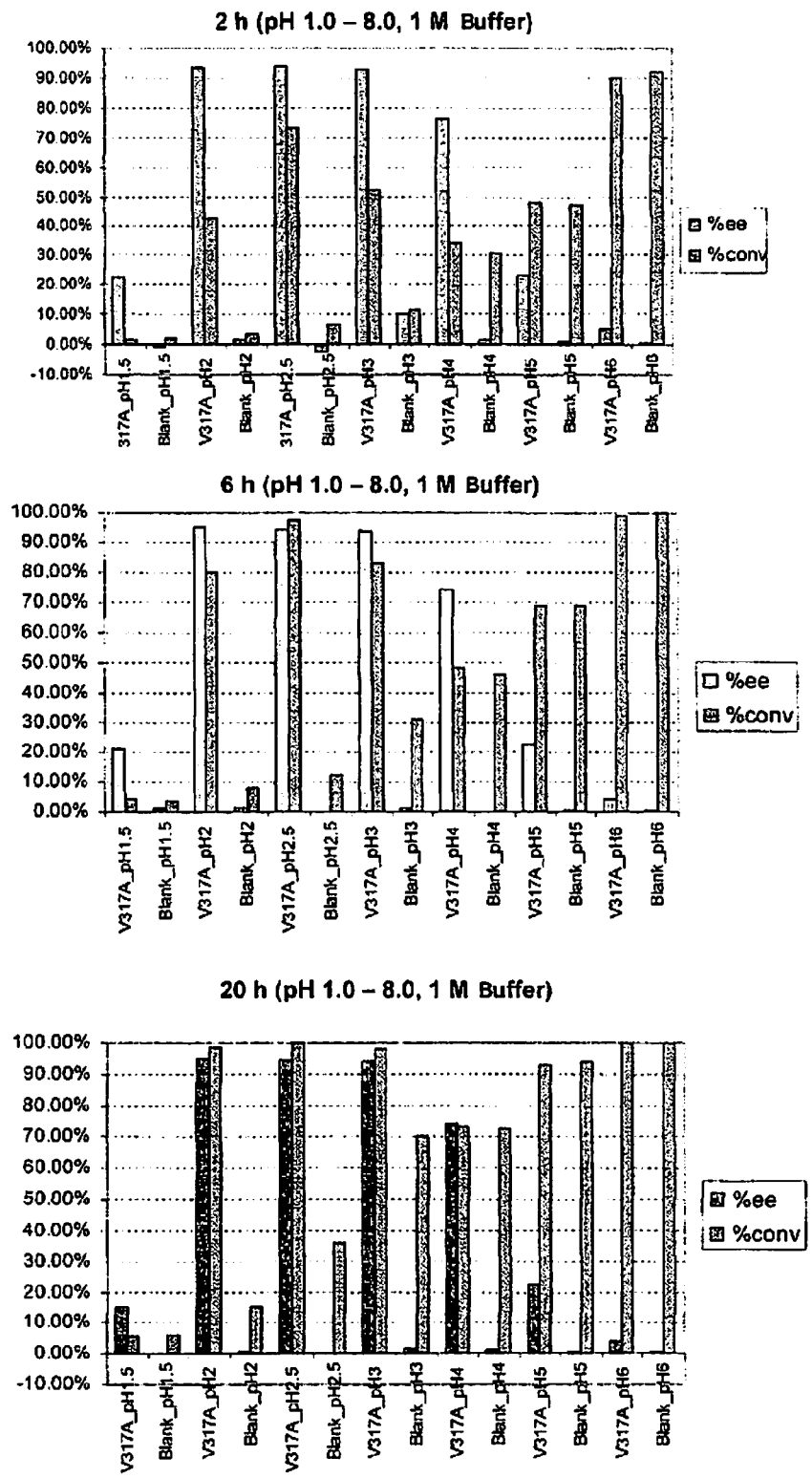
Figure 8: Conversion and enantiomeric excess for V317A at various pH values after 2h, 6h and 20h. A 1M potassium phosphate buffer was used.

R-HYDROXYNITRILE LYASE (R-HNL) RANDOM VARIANTS AND THEIR USE FOR PREPARING OPTICALLY PURE, STERICALLY HINDERED CYANOHYDRINS

CROSS REFERENCE TO RELATED APPLICATIONS

This application is a US filing under 35 USC 371 of PCT/EP2007/063692 filed on Dec. 11, 2007, which claims the benefit of AT A2064/2006 filed on Dec. 14, 2006 and EP 07016544.4 filed on Aug. 23, 2007, the contents of each of which are incorporated herein by reference.

Biocatalytic processes have become very important to the chemical industry. Of particular importance is the use of enzymes, when the properties of biocatalysts enable either of the two enantiomers in chemical reactions with chiral or prochiral compounds to be reacted or formed preferentially.

Essential requirements for utilizing these favorable properties of enzymes are their low-cost availability in sufficient amounts, as required in industrial processes, a sufficiently high reactivity, selectivity and high stability under the realistic conditions of an industrial process.

Cyanohydrins are a particularly interesting class of chiral chemical compounds. Cyanohydrins are important, for example, in the synthesis of α-hydroxy acids, α-hydroxy ketones, β-amino alcohols, etc., which are used for preparing biologically active substances, for example pharmaceutical active compounds, vitamins or pyrethroid compounds.

Cyanohydrins are prepared, for example, by way of addition of hydrocyanic acid to the carbonyl group of a ketone or aldehyde.

The industrial preparation of (S)-cyanohydrins, for example, has been made possible due to isolation of the enzyme *Hevea brasiliensis* S-hydroxynitrile lyase and is described inter alia in WO 97/03204, EP 0 951561 and EP 0 927766.

For a multiplicity of interesting chemical compounds, however, the R-enantiomers are important for industrial applications. In this context, processes for preparing a number of products have been described previously, which, however, can be employed only on a laboratory scale (e.g. EP 0 276375, EP 0 326063, EP 0 547655). This involved using mainly enzyme preparations obtained from plants of the Rosaceae family, for example from the kernels of almonds (*Prunus amygdalus*). Further examples of previously used R-HNLs are those from linseed seedlings (*Linum usitatissimum*; LuHNL), which have been cloned as the first R-HNL gene and expressed in *E. coli* and *Pichia pastoris*, or *Phlebodium aureum* R-HNLs.

The literature makes mention of low temperatures (e.g.: Persson et al.; Enzyme and Microbial Technology 30(7), 916-923; 2002), a pH below pH 4 (e.g.: Kragl et al.; Annals of the New York Academy of Science; 613 (Enzyme Eng. 10), 167-75, 1990) and the use of 2-phase systems (e.g.: EP 0 547655) or of emulsions (e.g.: EP 1 238094) as advantageous reaction parameters in order to be able to obtain products with high optical purity. The possibility of achieving very high enantiomeric excesses by applying greatly increased enzyme concentrations has also been described. For example, EP 0 528256 B1 used 20 mg or 2000 U of D-oxinitrilase EC 4.1.2.10 per mmol of hydroxypivalaldehyde.

Unfortunately, however, most native R-HNLs have half lives of less than one hour at a pH below 4.

EP 1 223220 A1 describes recombinant enzymes which are prepared by cloning a *Prunus amygdalus* gene coding for an R-HNL isoenzyme, for example for isoenzyme 5 (PaHNL5), and by heterologous expression in microbial hosts. As the examples reveal, said R-HNL is distinguished by a substantially increased stability at low pH compared with the other known R-HNLs.

Disadvantageously, substrate acceptance was found to be unsatisfactory, since some substrates are converted in the presence of, for example, recombinant PaHNL5 at a markedly lower reaction rate than in the presence of commercial, native plant R-HNL preparations from almond kernels.

Based on the 3D structural model of PaHNL5 and the corresponding enzyme-substrate complexes, it was possible to generate numerous PaHNL5 enzyme variants with improved substrate acceptance and thus increased activity and selectivity by structure-directed design (e.g.: WO 2004/083424, Angew. Chem. Int. Ed. Engl. 2003; 42, 4815, WO 2006/076965).

Thus, WO 2004/083424 describes mutants of said recombinant HNLs, in which a residue from the group consisting of alanine, phenylalanine, leucine or isoleucine in the active site is replaced with other residues, thereby increasing substrate acceptance, in particular for substituted benzaldehydes. One example is the A111G variant.

Furthermore, WO 2006/076965 describes mutants of the recombinant R-HNLs, which have improved substrate acceptance, increased activity and improved stereoselectivity, for example for substrates such as phenylpropionaldehyde or phenylpropenal. These variants were prepared by way of special mutations in R-HNLs of the Rosaceae family, such as, for example, PaHNL5 of EP 1 223220 A1, with a) the amino acid residue corresponding to position 360 of the mature PaHNL5 protein being substituted by a different apolar amino acid or a neutral amino acid and/or
b) the amino acid residue corresponding to position 225 of the mature PaHNL5 protein being substituted by a different polar amino acid, it optionally being possible for a further 1 to 20 residues in the active site or in the hydrophobic channel leading to the active site being substituted. One example is the V360I mutant.

The structural analysis of computer models of enzyme-substrate complexes, however, did not provide any further indications for improving the substrate acceptance of R-HNLs.

However, since this field still has a great need for enzymes that can be made available in sufficient amounts and in a cost-effective manner for industrial reactions on an industrial scale and that have improved substrate acceptance and thus increased activity, increased selectivity and also increased stability, it was the object of the invention to find new variants of R-hydroxynitrile lyases of the Rosaceae family which meet these requirements and can convert in particular sterically hindered, aliphatic carbonyl compounds and also substituted aromatic aldehydes in a more efficient and selective way than any previously known R-HNLs.

Surprisingly, this object was achieved by random mutations in R-hydroxynitrile lyases of the Rosaceae family, such as, for example, PaHNL5 of EP 1 223220 A1 or the PaHNL5 A111G mutant of WO 2004/083424.

The invention accordingly relates to R-hydroxynitrile lyases with improved substrate acceptance, increased activity and increased selectivity, obtainable by introducing random mutations with the aid of random mutagenesis and/or saturation mutagenesis techniques, identifying by means of screening or selection and, where appropriate, subsequently combining advantageous mutations.

The R-HNLs of the invention are prepared by random mutagenesis with the aid of methods of directed evolution.

One possibility of preparing and then analyzing novel biopolymers with improved properties is described, for example, in the theoretical paper by Henco and Eigen (WO 9218645). Directed evolution or laboratory evolution of biopolymers involves in principle imitating or copying methods of natural evolution in biological systems. Typical methods of producing diversity in enzyme libraries include random point mutagenesis, in vitro or in vivo recombination, random insertions and random deletions and the use of transposons.

Random point mutagenesis is carried out, for example, by means of error prone polymerase chain reaction (epPCR). This involves using either DNA polymerases with a high intrinsic error rate, such as, for example, Mutazyme® I DNA polymerase or Mutazyme® II DNA polymerase from Stratagene (CA, USA), or designing the conditions of said polymerase chain reaction in such a way that the error rate increases. The addition of divalent cations, a nucleotide imbalance, pH alteration or a combination of two or three of these options, result in suitable alterations in the PCR reaction mixture for DNA polymerases, such as, for example, Taq DNA polymerases from Qiagen, Fermentas, etc. or Hot Start Taq DNA polymerases from Fermentas or HotStarTaq DNA polymerases from Qiagen, etc., to incorporate errors with a controllable rate during amplification of the gene.

It is furthermore possible to use methods such as GSSM (gene site saturation mutagenesis) (DeSantis et al., J. Am. Chem. Soc., 2003, 125, 11476), SeSaM (sequence saturation mutagenesis) (Wong et al., Nucleic Acids Res, 2004, 32, E26; Wong et al., Anal Biochem, 2005, 341, 187), CASTing (complete active site saturation test) (Clouthier et al., J Org Chem, 2006, 71, 8431), chemical mutagenesis, mutator strains or physical methods or other saturation mutagenesis techniques known to the skilled worker, in order to enable enzyme libraries to be prepared in an efficient manner. Site-specific saturation mutagenesis in individual positions of the amino acid sequence may also be used for generating increased diversity. Furthermore, synthetic preparation of whole genes or individual sections thereof, for example, also allows production of suitable gene libraries.

The combination of advantageous mutations, introduction of synergistic effects by combining mutations or the removal of neutral or damaging mutations is carried out using recombinant techniques such as DNA shuffling (Stemmer, Nature, 1994, 370, 389), StEP (staggered extension process) (Zhao et al., Nat Biotechnol, 1998, 16, 258), RACHITT (random chimeragenesis on transient templates) (Coco et al., Nat Biotechnol, 2001, 19, 354), CLERY (combinatorial libraries enhanced by recombination in yeast) (Abécassis et al., Nucleic Acids Res, 2000, 28, E88), SHIPREC (sequence homology independent protein recombination) (Sieber et al., Nat Biotechnol, 2001, 19, 456), ITCHY (Incremental truncation for the creation of hybrid enzymes) (Ostermeier et al., Nat Biotechnol, 1999, 17, 1205; Lutz et al., Nucleic Acids Res, 2001, 29, E16; Ostermeier et al., Bioorg Med Chem, 1999, 7, 2139), SCRATCHY (Lutz et al., Proc Natl Acad Sci USA, 2001, 98, 11248), etc. However, additive and synergistic effects of mutations of individual enzyme variants may also be achieved by introducing mutations of one mutant into a second mutated nucleic acid, for example by means of site-specific mutagenesis, gene synthesis or overlap extension PCR.

Methods of introducing increased diversity in genes with directed evolution of enzymes usually result in insertions, deletions or point mutations in nucleic acid sequences.

At the amino acid level, these modifications result in insertion of amino acid residues, deletion of amino acid residues, reading frame shifts or replacement of one amino acid residue with another amino acid residue.

Furthermore, directed evolution methods introduce point mutations which result in "silent mutations", with the nucleic acid sequence being modified but said modification not causing the amino acid sequence to be modified. Owing to the partly different codon usage of the various organisms, silent mutations in heterologously expressed genes may generate nucleobase triplets which are either advantageous or disadvantageous for expression. This may either improve or worsen for example heterologous expression and also folding of active enzymes in the corresponding host organism.

Functional expression of enzyme libraries is carried out in heterologous or secretory expression systems, with preference being given to using organisms such as, for example, *Pichia pastoris*, *Saccharomyces cerevisiae*, *Kluyveromyces lactis*, *Aspergillus niger*, *Penicillium chrysogenum*, *Pichia methanolica*, *Pichia polymorpha*, *Hansenula polymorpha*, *Pichia anomala*, *Schizosaccharomyces pombe*, *Arxula adeninivorans*, *Yarrowia lipolytica*, *Bacillus subtilis*, *Pseudomonas fluorescens*, *Escherichia coli*, *Bacillus stearothermophilus*, *Thermus thermophilus*, *Streptomyces* sp. etc., particularly preferably *Escherichia coli*, *Saccharomyces cerevisiae*, *Kluyveromyces lactis* and *Pichia pastoris*.

The R-HNLs of the invention are variants of hydroxynitrile lyases of the Rosaceae family.

Preparation of the mutants of the invention may be based here on native R-HNLs of the Rosaceae family, such as, for example, R-HNLs of *Prunus amygdalus* (PaHNL), *Prunus serotina* (PsHNL), *Prunus avium*, *Prunus laurocerasus*, *Prunus lyonii*, *Prunus armaniaca*, *Prunus persica*, *Prunus domestica* (PdHNL), *Prunus mume* (PmHNL), *Malus communis*, *Malus pumila*, *Cyclonia oblonga* etc., or recombinant R-HNLs, for example of EP 1 223 220 or EP 1 566 441, and mutated recombinant R-HNLs such as, for example, recombinant PdHNLs or those of WO 2004/083424 or WO 2006/076965.

Preferred native R-HNLs used are R-HNLs of *Prunus amygdalus* (PaHNL), *Prunus serotina* (PsHNL), *Prunus domestica* (PdHNL) or *Prunus mume* (PmHNL). Preferred recombinant R-HNLs are recombinant R-HNLs of *Prunus domestica* (PdHNL), in particular PdHNL1, and the recombinant R-HNL described in EP 1 566 441 (PaHNL4) and the recombinant R-HNLs described in EP 1 223 220 (PaHNL1 to PaHNL5), with particular preference being given to recombinant PaHNL5.

A previously improved R-HNL mutant, for example of WO 2004/083424 or WO 2006/076965, may also serve as basis, with particular preference being given to the mutants A111G and V360I.

The R-HNL to be modified may also be present here in a modified sequence which is obtained, for example, by replacing the first amino acid(s) in the sequence or by removing the first amino acid(s) or by attaching further amino acids such as GluAlaGluAla, or by fusion with other isoenzymes. For example, individual R-HNL isoenzymes may be fused to other R-HNL isoenzymes or to proteins which facilitate secretory production.

It is also possible, prior to mutation, to replace the natural or plant signal sequence with another signal sequence, for example with the signal sequence of the *Saccharomyces cerevisiae* alpha mating factor (Alpha-MF), *Saccharomyces cerevisiae* invertase (SUC2), the *Pichia* killer toxin signal sequence, α-amylase, *Pichia pastoris* acid phosphatase (PHO1), *Phaseolus vulgaris* agglutinin (PHA-E); the *Aspergillus niger* glucoamylase signal sequence (glaA), the *Aspergillus niger* glucose oxidase signal sequence (GOX), the *Pichia pastoris* Sec10 signal sequence, the signal sequence of the 28 kD subunit of the *Kluyveromyces lactis* killer toxin, the BSA signal sequence, etc., or synthetic variants thereof, or else with synthetic consensus sequences. The signal sequences may also comprise point mutations, insertions or deletions.

Suitable signal sequences and their mutants are described, for example, in Heijne G. et al., FEBS Letters 244 (2), 439-46 (1989), EP 19911213, Paifer et al., Biotecnologia Aplicada 10(1), 41-46, (1993), Raemaekers et al., European Journal of Biochemistry 265(1), 394-403 (1999) etc.

Preference is given to replacing the plant signal sequence with the signal sequence of the *Saccharomyces cerevisiae* alpha mating factor or variants thereof (Xiong et al., J Biochem Mol Biol, 2004, 37, 282; Xiong et al., Appl Microbiol Biotechnol, 2006, 72, 1039).

The HNL enzyme libraries of the invention are preferably prepared by random point mutagenesis using either the recombinant R-HNLs described in EP 1 223 220 A1 (PaHNL1 to PaHNL5), with particular preference being given to recombinant PaHNL5, or a previously improved R-HNL mutant, for example of WO 2004/083424 or WO 2006/076965, with particular preference being given to the mutants A111G and V360I, as template. It is furthermore possible to use improved HNL variants resulting from mutagenesis and screening as template for preparing further improved variants, with preference being given to the variants I304VA111G, I108MA111G, N110SA111G, N3IA111G, I108MA111GY432FV424A, N3II108MA111G, I108MN110SA111G, I108MA111GN225S, I108MA111GV317A and V317A.

Random point mutagenesis is carried out, for example, by means of error prone PCR, either using polymerases with a high intrinsic error rate, such as, for example, Mutazyme®I DNA polymerase or Mutazyme® II DNA polymerase from Stratagene (CA, USA), or the conditions of the polymerase chain reaction are designed, due to the addition of divalent cations, a nucleotide imbalance, pH alteration or a combination of two or three of these options, in such a way that the error rate of the DNA polymerase used (for example Taq DNA polymerases from Qiagen, Fermentas, etc. or HotStar-Taq DNA polymerases from Qiagen, etc.) increases.

The template used here for random point mutagenesis by means of error prone PCR is either the nucleic acid sequence coding only for the mature HNL enzyme variants or the nucleic acid sequence coding for the mature HNL enzyme variants and the signal sequence, preferably of the *Saccharomyces cerevisiae* alpha mating factor.

The PahnI5- or PahnI5α-nucleic acid sequence modified by means of random point mutagenesis is then linked with the aid of overlap extension PCR to a left flanking end, for example the 3'-terminal end of a eukaryotic promoter (e.g.: GAP-promoter) with or without alpha-signal sequence, and a right flanking end coding, for example, for a selection marker (e.g.: zeocin resistance). These linear expression cassettes (FIG. 1A) are then transformed into *Pichia pastoris*. However, the mutated genes may also be cloned into a suitable expression vector. Such an expression vector is subsequently linearized and transformed into *Pichia pastoris* and integrated into the *Pichia* genome or the intact expression plasmids are transformed into *Pichia* and maintained in the cells via autonomous replication.

The HNL enzyme libraries of the invention are furthermore preferably prepared by site-specific saturation mutagenesis in individual positions of the amino acid sequence, applying the overlap extension PCR strategy to the preparation of said libraries. This results in expression cassettes for direct transformation into *Pichia pastoris*.

Firstly, 3 fragments are prepared by means of PCR, with the first fragment comprising, in addition to the 3'-terminal end of a eukaryotic promoter (e.g.: GAP promoter), also the alpha-signal sequence and a first section of the PahnI5 gene. Said fragment 1 extends up to the position in the PahnI5 gene, which is to be mutated. The second fragment extends from the primer at the site to be mutated to the end of the PahnI5 gene, and the third fragment codes for a selection marker (e.g.: zeocin resistance), for example. Said fragments possess nucleotide sequences which overlap each other and are subsequently assembled by means of overlap extension PCR. The strategy is also illustrated in FIG. 1B.

The identification of novel, improved enzyme variants is carried out with the aid of suitable high throughput screening or selection methods which allow the desired variants to be detected rapidly and reliably. An important guideline for the application of methods of directed evolution is the fact that 'You get what you screen for' (Arnold, Acc Chem Res, 1998, 31, 125), meaning that it is generally desirable to use a screening substrate which resembles the actually interesting substrate as much as possible, more specifically which corresponds to the actual substrate.

Any conceivable chemical reaction may then be transformed into either a high throughput screening method or a high throughput selection method.

Thus it is possible to carry out high throughput screening or high throughput selection methods with a suitable nitrile, a suitable aldehyde or a suitable ketone as substrate, with either cleavage of the nitrile being monitored or conversion of the corresponding aldehyde or ketone to the corresponding cyanohydrins being analyzed.

Frequent use is made of reactions with chromogenic or fluorogenic compounds for high throughput assays (Goddard and Reymond, Trends Biotechnol, 2004, 22, 363). Some of these substrates are absorbed by living cells and employed for monitoring the conversion in vivo. The best known example is X-Gal, a β-galactoside which is cleaved by a β-galactosidase and in the process releases the insoluble indigo dye (Pearson et al., Lab Invest, 1963, 12, 1249).

Another general concept includes carrying out a second reaction with a reaction partner of the first reaction actually to be analyzed, in order to generate a measurable signal. This concept is used, for example, for detecting aldehydes. The carbonyl functionality is detected here, for example, by using a colorimetric Schiff base reagent (Doderer et al., Anal Biochem, 2003, 321, 131). A fluorimetric assay is employed inter alia for reacting aldehydes with 4-hydrazino-7-nitrobenzofurazanes (NBDHs) to give the corresponding, highly fluorescent hydrazone which can be quantified by means of fluorescence measurement (Bornscheuer, Eng Life Sci, 2004, 4, 539; Konarzycka-Bessler and Bornscheuer, Angew Chem Int Ed, 2003, 42, 1418; Koizumi and Suzuki, J Chromatogr, 1988, 457, 299).

Other methods for analyzing high throughput reactions include HPLC, GC, MS and capillary electrophoresis methods. To detect enantioselectivities in high throughput experiments, for example, GC methods using chiral columns are used or isotope-labeled substrates are employed which enable the enantiomer substrate or product to be analyzed by means of mass spectrometry (Reetz et al., Angew Chem Int Ed, 1999, 38, 1758), $^1$H-NMR (Reetz et al., Adv Synth Catal, 2002, 344, 1008) or FTIR spectroscopy (Tielmann et al., Chemistry, 2003, 9, 3882).

HNL enzyme activities of the HNL enzyme variants of the invention are determined using substrates such as, for example, mandelonitrile or 2-chloromandelonitrile, monitoring photometrically cleavage to the corresponding aldehyde and HCN (Weis et al., J Mol Catal B: Enzym, 2004, 29, 211).

Conversion of hydroxypivalaldehyde using the HNL enzyme variants of the invention is analyzed either by determining the turnover by way of reacting the remaining aldehyde with 4-hydrazino-7-nitrobenzofurazane (NBDH) or by determining the enantiomeric excess after derivatization of the reaction mixture by means of GC on a cyclodextrin column (CP-Chirasil-Dex CB).

The improved HNL variants obtained by the first round of screening are repeatedly examined by means of rescreening which is carried out in a similar manner to the screening of the first round.

The amino acid residues in HNL muteins having improved properties and obtained by said screening, corresponding to position 3 and/or position 108 and/or position 110 and/or position 304 and/or position 424 and/or position 432 of the mature PaHNL5A111G protein of WO 2004/083424, are replaced with a different amino acid, for example with alanine, isoleucine, methionine, serine, phenylalanine or valine. Furthermore, the amino acid residue corresponding to position 317 of the mature PaHNL5 protein of WO 2004/083424 is replaced with a different amino acid, for example with alanine. The found HNL mutein of the invention with the mutation in position V317A here differs from the variant in WO 2004/083424 in that the GTA (valine) codon has not been replaced with GCT (alanine) but with the GCA (alanine) codon which is particularly preferred for expression in *Pichia pastoris*. Unexpectedly, positive effects in the conversion of sterically hindered, aliphatic substrates are observed here.

Furthermore, the nucleobase triplets corresponding to amino acids positions 85 and/or 209 and/or 278 and/or 432 in the HNL muteins with improved properties, obtained by the screening, are replaced with other codons coding for the same amino acid in each case (silent mutation).

In order to improve expression of heterologous genes, particularly preferably of PaHNL5 muteins in *Pichia pastoris*, firstly chaperones or other helper proteins, for example a protein disulfide isomerase (PDI) of *Pichia pastoris* or *Saccharomyces cerevisiae* may be coexpressed (Inan et al., Biotechnol Bioeng, 2006, 93, 771; Zhang et al, Biotechnol. Progress, 2006, 22, 1090), with secondly an attempt being made to transfer the codon usage of the host organism optimally to the corresponding gene to be expressed heterologously. Codon usage of the Pahnl5 gene is improved by employing DNA optimization programs such as, for example, Leto 1.0 by Entelechon (Regensburg, D). For calculation, either the known codon usage tables for the corresponding host organisms (Codon Usage Database) are used or own codon usage tables of specific genes highly expressed by the host organism, for example (e.g.: alcohol oxidase 1 in *Pichia pastoris*), are calculated. Based on the genes calculated by means of DNA optimization software, firstly oligonucleotides are designed which are then used for synthesis of the corresponding gene.

Usable proteins are obtained by further processing according to the references cited above.

The R-HNL mutants of the invention are suitable for preparing enantiomerically pure cyanohydrins, in particular sterically hindered aliphatic and substituted aromatic cyanohydrins, with increased rate of conversion, activity and selectivity over the prior art.

The invention accordingly further relates to the use of the R-HNL mutants of the invention for preparing enantiomerically pure cyanohydrins.

For example, R-HNL variants may be used for enantioselective cleavage of cyanohydrins.

More specifically, the R-HNL mutants of the invention are employed in the addition of hydrocyanic acid to aliphatic and aromatic aldehydes or ketones as substrates.

Aldehydes here mean aliphatic, aromatic or heteroaromatic aldehydes. Aliphatic aldehydes here mean saturated or unsaturated, aliphatic, straight-chain, branched or cyclic aldehydes. Preferred aliphatic aldehydes are straight-chain or branched aldehydes having in particular from 2 to 30 carbon atoms, preferably from 4 to 18 carbon atoms, which are saturated or mono- or polyunsaturated in from 1 to 6 positions. Said aldehyde may have both C—C double bonds and C—C triple bonds. Furthermore, the aliphatic, aromatic or heteroaromatic aldehydes may be unsubstituted or substituted by groups which are inert under the reaction conditions, for example by optionally substituted aryl or heteroaryl groups such as phenyl, phenoxy or indolyl groups, by halogen, hydroxy, hydroxy $C_1$-$C_5$ alkyl, $C_1$-$C_5$ alkoxy, $C_1$-$C_5$ alkylthio, ether, alcohol, carboxylate, nitro or azido groups.

Examples of preferred aliphatic aldehydes are hydroxypivalaldehyde, pivalaldehyde, propionaldehyde, butyraldehyde, hexanal, isobutyraldehyde, isovaleraldehyde, acrolein, crotonaldehyde, methacrolein, 3-phenylpropanal, 3-phenylpropenal (cinnamaldehyde), 3-phenylpropynal, etc.

Examples of aromatic or heteroaromatic aldehydes are benzaldehyde and differently substituted benzaldehydes such as, for example, 2-chlorobenzaldehyde, 3-chlorobenzaldehyde, 4-chlorobenzaldehyde, 2-bromobenzaldehyde, 3-bromobenzaldehyde, 4-bromobenzaldehyde, 2-fluorobenzaldehyde, 3-fluorobenzaldehyde, 4-fluorobenzaldehyde, 3,4-difluorobenzaldehyde, 3-phenoxybenzaldehyde, 4-fluoro-3-phenoxybenzaldehyde, 2-hydroxybenzaldehyde, 3-hydroxybenzaldehyde, 4-hydroxybenzaldehyde, 2-methoxybenzaldehyde, 3-methoxybenzaldehyde, 4-methoxybenzaldehyde, furthermore furfural, methylfurfural, anthracene-9-carbaldehyde, furan-3-carbaldehyde, indole-3-carbaldehyde, naphthalene-1-carbaldehyde, phthaldialdehyde, pyrazole-3-carbaldehyde, pyrrole-2-carbaldehyde, thiophene-2-carbaldehyde, isophthalaldehyde or pyridinealdehydes, thienylaldehydes etc.

Ketones are aliphatic, aromatic or heteroaromatic ketones in which the carbonyl carbon substituents are the same or different. Aliphatic ketones mean saturated or unsaturated, straight-chain, branched or cyclic ketones. The ketones may be saturated or mono- or polyunsaturated. They may be unsubstituted or substituted by groups which are inert under reaction conditions, for example by optionally substituted aryl or heteroaryl groups such as phenyl or indolyl groups, by halogen, ether, alcohol, carboxylate, nitro or azido groups.

Examples of aromatic or heteroaromatic ketones are acetophenone, indolylacetone etc. Examples of aliphatic ketones are acetone, dihydroxyacetone, butanone, butenone, 3-methylbutanone, 3,3-dimethylbutanone, 2-pentanone, 4-methylpentanone, 5-chloro-2-pentanone, 2-hexanone, 5-methylhexan-2-one, 2-heptanone, 2-octanone, 3-octanone, etc.

Aldehydes and ketones which are suitable according to the invention either are known or can be prepared in the usual manner.

The substrates are reacted with a cyanide group donor in the presence of the HNLs of the invention.

Suitable cyanide group donors are hydrocyanic acid, alkaline metal cyanides or a cyanohydrin of the general formula I $$R_1R_2C(OH)(CN),$$

wherein $R_1$ and $R_2$ independently of one another are hydrogen or an unsubstituted hydrocarbon group, or $R_1$ and $R_2$ are together an alkylene group having 4 or 5 carbon atoms, with $R_1$ and $R_2$ not being hydrogen at the same time. The hydrocarbon groups are aliphatic or aromatic, preferably aliphatic, groups. $R_1$ and $R_2$ are preferably alkyl groups having from 1-6 carbon atoms, with very particular preference being given to the cyanide group donor being acetone cyanohydrin.

The cyanide group donor may be prepared by known processes. Cyanohydrins, in particular acetone cyanohydrin, can also be obtained commercially.

Preference is given to using hydrocyanic acid (HCN), KCN, NaCN, or acetone cyanohydrin, particularly preferably hydrocyanic acid, as cyanide group donor.

Hydrocyanic acid may in this context also be released from one of its salts such as, for example, NaCN or KCN only shortly before the reaction and added to the reaction mixture in undiluted or dissolved form.

The conversion can be carried out in an organic system, aqueous system or 2-phase system or in emulsified and also in undiluted form.

The aqueous system used is an aqueous solution or buffer solution comprising the HNL of the invention. Examples of this are sodium citrate buffer, citrate-phosphate buffer, phosphate buffer, etc.

Organic diluents which may be used are aliphatic or aromatic hydrocarbons which are slightly miscible or immiscible with water and which are optionally halogenated, alcohols, ethers or esters or mixtures thereof, or the substrate itself. Preference is given to employing DMF, ethanol, isopropanol, isobutanol, toluene, xylols, mesitylene, cumene methyl tert-butyl ether (MTBE), diisopropyl ether, dibutyl ether, diethyl ether, dimethyl ether and ethyl acetate or a mixture thereof.

The HNLs of the invention may be present here either as such or in immobilized form, for example on a support such as Celite®, Avicel, etc. or as "cross-linked enzyme aggregate" (CLEA) in the organic diluent, but conversion may also be carried out in a two-phase system or in emulsion, using non-immobilized HNL.

The conversion is carried out here at temperatures of from −10° C. to +50° C., preferably from −5° C. to +45° C., particularly preferably from 0° C. to 25° C.

The pH of the reaction mixture may be from 1.8 to 7, preferably from 2 to 5, and particularly preferably from 2.0 to 3.5.

EXAMPLE 1

Preparation of Random Mutations in R-Hydroxynitrile Lyases by Error Prone Polymerase Reactions Expression libraries of R-HNL genes containing random mutations were prepared with the aid of overlap extension PCR, with the middle fragment of the mutated PaHNL5 sequence (PCR IIa or IIb) and the left flanking end consisting for example, of the 3'-terminal end of a eukaryotic promoter (PCR I) (e.g.: GAP promoter), while the right flanking end codes for a selection marker (e.g.: zeocin resistance) (PCR III). FIG. 1A depicts this linear expression cassette.

PCR I:

Fragment 1 (3'-terminal end of the GAP promoter) was amplified either from the pGAPZAPaHNL5αL1Q, A111G plasmid (corresponds to pGAPPamHNL5a of EP 1 223220 A1, with the additional mutations L1Q and A111G, described in EP 1 223220 A1 and, respectively, WO 2004/083424, Angew Chem Int Ed Engl, 2003, 42, 4815) using the pGAP158for/HNL5alpha21aq primer pair, or from the pGAPPamHNL5a plasmid of EP 1 223220 A1, using the pGAP158for/pGAPZA484r primer pair.

The PCR was carried out in a 100 μl reaction volume (60 ng of plasmid DNA, 1× Phusion HF buffer, 0.2 mM dNTPs, 0.4 μM of each primer, 1.2 U of Phusion High-Fidelity DNA polymerase from Finnzymes (Cat. No. F530L)) in an Applied Biosystems thermocycler.

A denaturing step of 30 s at 98° C. was followed by 30 cycles of amplification (10 s at 98° C., 20 s at 60° C., 1 min at 72° C.) and a final step of 7 min at 72° C.

After the PCR, the DNA template was removed by means of DpnI digestion. The PCR product was then purified either by means of the QIAquick PCR Purification Kit from Qiagen (Cat. No. 28106) or according to the purification protocol of the QIAquick Gel Extraction Kit (Cat. No. 27106).

PCR IIa:

Preparation of random mutations in R-hydroxynitrile lyases by error prone polymerase chain reaction (epPCR) by means of poisoned HotStarTaq DNA polymerase In each case 10 ng of the expression plasmids pGAPPamHNL5a (EP 1 223220 A1), pGAPPamHNL5aV317A (corresponds to pGAPPamHNL5a of EP 1 223220 A1, containing the additional mutation V317A (GTA→GCT)) and pGAPZAPaHNL5αL1Q, A111G (corresponds to pGAPPamHNL5a of EP 1 223220 A1, containing the additional mutations L1Q and A111G, described in EP 1 223220 A1 and, respectively, WO 2004/083424, Angew Chem Int Ed Engl, 2003, 42, 4815) were used as template for the mutagenesis reaction by means of poisoned HotStarTaq DNA polymerase from Qiagen (Cat. No. 203205).

A 100 μl reaction mixture (1×PCR buffer, 0.2 mM dNTPs, 0.8 mM dCTP/dTTP mixture, 5.5 mM $MgCl_2$, 0.3 μM of each primer, and 5 U of HotStarTaq DNA polymerase from Qiagen) was prepared for the PCR. In addition, different $MnCl_2$ concentrations were employed (0 mM, 0.05 mM and 0.1 mM $MnCl_2$). The PCR was carried out in an Applied Biosystems (Forster City, Calif.) thermocycler. The HNL5alpha11q/PaHNL5endBr primer pair was used for the pGAPZAPaHNL5αL1Q, A111G plasmid. The pGAPZA484f/PaHNL5endBr primer pair was used for expression plasmids such as pGAPPamHNL5a or pGAPPamHNL5aV317A.

The following temperature program was used:

A) Denaturation at 95° C. for 15 min

B) 30 cycles of 50 s at 94° C., 30 s at 60° C. and 2 min at 72° C.

C) Extension at 72° C. for 7 min.

The PCR was followed by removing the DNA template by means of DpnI digestion. For this, 2 μl of DpnI (10 U/μl) were added to the 100 μl PCR mixture, and the mixture was incubated at 37° C. for 2-3 h. The PCR product was then purified either by means of the QIAquick PCR Purification Kit from Qiagen (Cat. No. 28106) or according to the purification protocol of the QIAquick Gel Extraction Kit (Cat. No. 27106).

PCR IIb:

Preparation of random mutations in R-hydroxynitrile lyases by error prone polymerase chain reaction (epPCR) by means of the GeneMorph® Random Mutagenesis Kit from Stratagene (Cat. #600550)

In each case 50-100 ng of the expression plasmids pGAPPamHNL5a (EP 1 223220 A1) and pGAPPamHNL5aV317A were used as template for the mutagenesis reaction by means of the GeneMorph® Random Mutagenesis Kit from Stratagene (Cat. #600550). In each case 40 pmol of the forward primer pGAPZA484f and 40 pmol of the reverse primer PaHNL5endBr were used for the PCR in 100 µl reaction mixtures. The PCR was carried out in an Applied Biosystems (Forster City, Calif.) thermocycler. A denaturing step of 30 s at 95° C. was followed by 25 cycles of amplification (30 s at 95° C., 30 s at 60° C., 4 min 30 s at 72° C.) and a final step at 72° C. for 10 min.

The PCR was followed by removing the DNA template by means of DpnI digestion. The PCR product was then purified according to the purification protocol of the QIAquick Gel Extraction Kit (Cat. No. 27106).

PCR III:

Fragment 3 which codes for zeocin resistance was amplified from the pGAPZAPaHNL5αL1Q, A111G plasmid (corresponds to pGAPPamHNL5a of EP 1 223220 A1, with the additional mutations L1Q and A111G, described in EP 1 223220 A1 and, respectively, WO 2004/083424, Angew Chem Int Ed Engl, 2003, 42, 4815) or the pGAPPamHNL5a plasmid (EP 1 223220 A1) using the PaHNL4L1Qendf3/Ocyclermrv1 primer pair.

The PCR was carried out in a 100 µl reaction volume (60 ng of plasmid DNA, 1× Phusion HF buffer, 0.2 mM dNTPs, 0.4 µM of each primer, 1.2 U of Phusion High-Fidelity DNA polymerase from Finnzymes (Cat. No. F530L)) in an Applied Biosystems thermocycler.

A denaturing step of 30 s at 98° C. was followed by 30 cycles of amplification (10 s at 98° C., 20 s at 60° C., 1 min at 72° C.) and a final step of 7 min at 72° C.

After the PCR, the DNA template was removed by means of DpnI digestion. The PCR product was then purified either by means of the QIAquick PCR Purification Kit from Qiagen (Cat. No. 28106) or according to the purification protocol of the QIAquick Gel Extraction Kit (Cat. No. 27106).

Assembly of the Linear Expression Cassette:

Assembly by means of overlap extension PCR was carried out in 2 steps.

In step 1, approx. 6 ng of the product of PCR I, approx. 30 ng of the product of PCR IIa or of PCR IIb, and approx. 25 ng of the product of PCR III were used as template and at the same time as primers for completing a contiguous product. Extension was carried out in a 50 µl reaction mixture containing 1× Phusion HF buffer, 0.2 mM dNTPs and 0.6 U of Phusion High-Fidelity DNA Polymerase from Finnzymes (Cat. No. F530L)) in an Applied Biosystems thermocycler. A denaturing step of 30 s at 98° C. was followed by 10 cycles of amplification (10 s at 98° C., 20 s at 60° C., 1 min at 72° C.) and a final step at 72° C. for 7 min.

In step 2, the following components were added to the PCR mixture of step 1: 34.7 µl of water (purest quality), 10 µl of 5× Phusion HF buffer, 1 µl of 10 mM dNTPs, 2 µl of pGAP158for primer (20 pmol/µl), 2 µl of Ocyclermrv1 primer (20 pmol/µl) and 0.6 U of Phusion High-Fidelity DNA Polymerase from Finnzymes (Cat. No. F530L). The mixture was denatured at 98° C. for 30 s. This was followed by 20 cycles of amplification (10 s at 98° C., 20 s at 60° C., 1 min at 72° C.) and a final step at 72° C. for 7 min.

Transformation of the Linear Expression Cassettes into *Pichia pastoris*:

The overlap extension PCR products were purified according to the purification protocol of the QIAquick PCR Purification Kit from Qiagen (Cat. No. 28106) or the QIAquick Gel Extraction Kit (Cat. No. 27106). This was followed by restriction by means of BlnI (AvrII) (Roche, Cat. #11558161001) or XmaJI (AvrII) (Fermentas, Cat. #ER1561). The cleavage reaction mixture was purified by means of ethanol precipitation, and approx. 1 µg of the prepared DNA was then transformed into *Pichia pastoris* X33 according to the Invitrogen standard protocol. 1 µg of DNA yielded 1000-6000 transformants.

```
Primer sequences:
HNL5alpha11q:
                                           (SEQ ID NO: 1)
5'-AGAGAGGCTGAAGCTCAAGCCAATACTTCTGCTCATGAT-3'

HNL5alpha21aq:
                                           (SEQ ID NO: 2)
5'-GAAGTATTGGCTTGAGCTTCAGCCTCTCTTTTCTCG-3'

Ocyctermrv1:
                                           (SEQ ID NO: 3)
5'-TGCTCACATGTTGGTCTCCAGCTTGC-3'

PaHNL4L1Qendf3:
                                           (SEQ ID NO: 4)
5'-GTCAGATAGCGAGGTCACTCAGTCCGAACAAAAACTCATCTCAGAA
G-3'

PaHNL5endBr:
                                           (SEQ ID NO: 5)
5'-GACTGAGTGACCTCGCTATCTGACTCACATGGACTCTTGAAT-3' pGAP158for:
                                           (SEQ ID NO: 6)
5'-CCTTCTCTCTCCTTCCACC-3' pGAPZA484f:
                                           (SEQ ID NO: 7)
5'-TTCGAAACGAGGAATTCACGATGAG-3' pGAPZA484r:
                                           (SEQ ID NO: 8)
5'-CTCATCGTGAATTCCTCGTTTCGAA-3'
```

EXAMPLE 2

Generation of Random Mutations in R-Hydroxynitrile Lyases by Means of Saturation Mutagenesis Saturation mutagenesis libraries of R-hydroxynitrile lyases were prepared by applying the strategy of an overlap extension PCR in order to obtain expression cassettes for direct transformation into *Pichia pastoris*. Initially 3 fragments were prepared by means of PCR. Owing to overlapping nucleotide sequences it was then possible to assemble said fragments by means of overlap extension PCR. The strategy is also illustrated in FIG. 1B.

PCRI:

The first fragment of this example comprises in addition to the 3'-terminal end of the GAP promoter also the alpha-signal sequence and a first section of the Pahnl5 gene. Fragment 1 extends to the position in the Pahnl5 gene that is to be mutated.

In each case 60 ng of the expression plasmids pGAPPamHNL5a (EP 1 223220 A1), pGAPPamHNL5aV317A (corresponds to pGAPPamHNL5a of EP 1 223220 A1, containing the additional mutation V317A (GTA→GCT)) and pGAPZAPaHNL5αL1Q, A111G (corresponds to pGAPPamHNL5a of EP 1 223220 A1, containing the additional mutations L1Q and A111G, described in EP 1 223220 A1 and, respectively, WO 2004/083424, Angew Chem Int Ed Engl, 2003, 42, 4815) were used as template for the PCR.

A 100 µl PCR mixture (1×HF Phusion buffer, 0.2 mM dNTPs, 0.4 µM of each primer, 1.2 U of Phusion DNA Polymerase from Finnzymes (Cat. No. F530L)) was prepared and the PCR was carried out in an Applied Biosystems (Forster City, Calif.) thermocycler. The pGAP158for N113XIongrev primer pair was used for saturation mutagenesis in position V113. The pGAP158for N317Xshortrev primer pair was used for saturation mutagenesis in position V317. The pGAP158for N329Xshortrev primer pair was used for saturation mutagenesis in position V329. The pGAP158for N360Xshortrev primer pair was used for saturation mutagenesis in position V360, and the pGAP158for/A111rev primer pair was used for combined saturation mutagenesis in positions N110 and G112.

The following temperature program was used:
A) Denaturation at 98° C. for 30 s
B) 30 cycles of 10 s at 98° C., 20 s at 60° C. and 1 min at 72° C.
C) Extension at 72° C. for 7 min.

The PCR was followed by removing the DNA template by means of DpnI digestion. For this, 2 µl of DpnI (10 U/µl) were added to the 100 µl PCR mixture, and the mixture was incubated at 37° C. for 2-3 h. The PCR product was then purified either by means of the QIAquick PCR Purification Kit from Qiagen (Cat. No. 28106) or according to the purification protocol of the QIAquick Gel Extraction Kit (Cat. No. 27106).

PCRII:

The second fragment extends from the primer at the site to be mutated to the end of the PahnI5 gene. In each case 60 ng of the expression plasmids pGAPPamHNL5a (EP 1 223220 A1), pGAPPamHNL5aV317A (corresponds to pGAPPamHNL5a of EP 1 223220 A1, containing the additional mutation V317A (GTA→GCT)) and pGAPZAPaHNL5αL1Q, A111G (corresponds to pGAPPamHNL5a of EP 1 223220 A1, containing the additional mutations L1Q and A111G, described in EP 1 223220 A1 and, respectively, WO 2004/083424, Angew Chem Int Ed Engl, 2003, 42, 4815) were used as template for the PCR.

100 µl PCR mixtures were prepared (1×HF Phusion buffer, 0.2 mM dNTPs, 0.4 µM of each primer, 1.2 U of Phusion DNA Polymerase from Finnzymes (Cat. No. F530L)), and the PCR was carried out in an Applied Biosystems (Forster City, Calif.) thermocycler. The V113Xshortfwd/PaHNL5endBr primer pair was used for saturation mutagenesis in position V113. The V317XIongfwd/PaHNL5endBr primer pair was used for saturation mutagenesis in position V317. The V329XIongfwd/PaHNL5endBr primer pair was used for saturation mutagenesis in position V329. The V360XIongfwd/PaHNL5endBr primer pair was used for saturation mutagenesis in position V360, and the A111Mutfor/PaHNL5endBr primer pair was used for combined saturation mutagenesis in positions N110 and G112.

A denaturating step of 30 s at 98° C. was followed by 30 cycles of amplification (10 s at 98° C., 20 s at 60° C., 1 min at 72° C.) and a final step at 72° C. for 7 min.

The PCR was followed by removing the DNA template by means of DpnI digestion. For this, 2 µl of DpnI (10 U/µl) were added to the 100 µl PCR mixture, and the mixture was incubated at 37° C. for 2-3 h. The PCR product was then purified either by means of the QIAquick PCR Purification Kit from Qiagen (Cat. No. 28106) or according to the purification protocol of the QIAquick Gel Extraction Kit (Cat. No. 27106).

PCRIII:

Fragment 3 which codes for zeocin resistance was amplified either from the pGAPZAPaHNL5αL1Q, A111G plasmid (corresponds to pGAPPamHNL5a of EP 1 223220 A1, with the additional mutations L1Q and A111G, described in EP 1 223220 A1 and, respectively, WO 2004/083424, Angew Chem Int Ed Engl, 2003, 42, 4815) or the pGAPPamHNL5a plasmid (EP 1 223220 A1), using the PaHNL4L1Qendf3/0cyclermrv1 primer pair.

The PCR was carried out in a 100 µl reaction volume (60 ng of plasmid DNA, 1× Phusion HF buffer, 0.2 mM dNTPs, 0.4 µM of each primer, 1.2 U of Phusion High-Fidelity DNA polymerase from Finnzymes (Cat. No. F530L)) in an Applied Biosystems thermocycler.

A denaturing step of 30 s at 98° C. was followed by 30 cycles of amplification (10 s at 98° C., 20 s at 60° C., 1 min at 72° C.) and a final step of 7 min at 72° C.

After the PCR, the DNA template was removed by means of DpnI digestion. The PCR product was then purified either by means of the QIAquick PCR Purification Kit from Qiagen (Cat. No. 28106) or according to the purification protocol of the QIAquick Gel Extraction Kit (Cat. No. 27106).

Assembly of the Linear Expression Cassette:

Assembly by means of overlap extension PCR was carried out in 2 steps.

In step 1, 45-60 ng of the product of PCR 1, 25-50 ng of the product of PCR II and 25-30 ng of the product of PCR III were used as template and at the same time as primers for completing a contiguous product. Extension was carried out in a 50 µl reaction mixture containing 1× Phusion HF buffer, 0.2 mM dNTPs and 0.6 U of Phusion High-Fidelity DNA Polymerase from Finnzymes (Cat. No. F530L)) in an Applied Biosystems thermocycler. A denaturing step of 30 s at 98° C. was followed by 10 cycles of amplification (10 s at 98° C., 20 s at 60° C., 1 min at 72° C.) and a final step at 72° C. for 7 min.

In step 2, the following components were added to the PCR mixture of step 1: 34.7 µl of water (purest quality), 10 µl of 5× Phusion HF buffer, 1 µl of 10 mM dNTPs, 2 µl of pGAP158for primer (20 pmol/µl), 2 µl of Ocyclermrv1 primer (20 pmol/µl) and 0.6 U of Phusion High-Fidelity DNA Polymerase from Finnzymes (Cat. No. F530L). The mixture was denatured at 98° C. for 30 s. This was followed by 20 cycles of amplification (10 s at 98° C., 20 s at 60° C., 1 min at 72° C.) and a final step at 72° C. for 7 min.

Transformation of the Linear Expression Cassettes into *Pichia pastoris*:

The overlap extension PCR products were purified according to the purification protocol of the QIAquick PCR Purification Kit from Qiagen (Cat. No. 28106) or the QIAquick Gel Extraction Kit (Cat. No. 27106). This was followed by digestion by means of BlnI (AvrII) (Roche, Cat. #11558161001) or XmaJI (AvrII) (Fermentas, Cat. #ER1561). The cleavage reaction mixture was purified by means of ethanol precipitation, and approx. 1 µg of the prepared DNA was then transformed into *Pichia pastoris* X33 according to the Invitrogen standard protocol. 1 µg of DNA yielded 1000-6000 transformants.

```
Primer sequences:
A111Mutfor:
                                              (SEQ ID NO: 9)
5'-ATCCTCGGTGGCACGACCATAATCNNKGGANNKGTCTACGCCAGA
GCTAACA-3'

A111rev:
                                              (SEQ ID NO: 10)
5'-GATTATGGTCGTGCCACCGAGGATC-3'

Ocyctermrv1:
                                              (SEQ ID NO: 3)
5'-TGCTCACATGTTGGTCTCCAGCTTGC-3'

PaHNL4L1Qendf3:
                                              (SEQ ID NO: 4)
5'-GTCAGATAGCGAGGTCACTCAGTCCGAACAAAAACTCATCTCAGAA
G-3'
```

-continued

PaHNL5endBr:
(SEQ ID NO: 5)
5'-GACTGAGTGACCTCGCTATCTGACTCACATGGACTCTTGAAT-3' pGAP158for:
(SEQ ID NO: 6)
5'-CCTTCTCTCTCCTTCCACC-3'

V113Xshortfwd:
(SEQ ID NO: 11)
5'-TACGCCAGAGCTAACATTTCATTC-3'

V113Xlongrev:
(SEQ ID NO: 12)
5'-GAATGAAATGTTAGCTCTGGCGTAMNNGCCTGCATTGATTATGGTCGTGCC-3'

V317Xlongfwd:
(SEQ ID NO: 13)
5'-CCCAAATCCAATTGAAGCCTCTGTTNNKACTGTTTTAGGCATTAGAAGTGATTATTATCAAG-3'

V317Xshortrev:
(SEQ ID NO: 14)
5'-AACAGAGGCTTCAATTGGATTTGG-3'

V329Xlongfwd:
(SEQ ID NO: 15)
5'-CTGTTTTAGGCATTAGAAGTGATTATTATCAANNKTCTCTGTCAAGCTTGCCATTTTCC-3'

V329Xshortrev:
(SEQ ID NO: 16)
5'-TTGATAATAATCACTTCTAATGCCTAAAACAG-3'

V360Xlongfwd:
(SEQ ID NO: 17)
5'-CCAAATTCGACTTTTGCTCATATTNNKAGCCAAGTTCCAGGACCATTGT-3'

V360Xshortrev:
(SEQ ID NO: 18)
5'-AATATGAGCAAAAGTCGAATTTGG-3'

EXAMPLE 3

Cultivation of *Pichia pastoris* Transformants in Deep Well Plates and Screening of PaHNL5 Mutants A) Search for improved activity of converting (R)-2-chloromandelonitrile:

400 µl of BM5D medium (0.2 M potassium phosphate, pH 6.0; 13.4 g/l yeast nitrogen base; 50 g/l D-glucose; 0.4 mg/l biotin) in 2 ml deep well plates were inoculated with single colonies of transformants and incubated with shaking at 320 rpm and 28° C., 80% humidity. After an incubation period of 96 hours, the cells were removed by centrifugation and the culture supernatant was used directly for measuring enzyme activity.

The activity assay was carried out in 96 well PS microtiter plates (Greiner Bio-One GmbH, D; Cat. No. 655101). Into each well 130 µl of 0.1 M phosphate-citrate buffer (pH 5.0) were introduced and then admixed with 20 µl of a suitable dilution of culture supernatant. The enzyme reaction was started by adding 50 µl of substrate solution (10 mg/ml (R)-2-chloromandelonitrile in 0.1M phosphate-citrate buffer (pH 3.5)). The slope of the absorbance profile at 300 nm was monitored on a Plate Reader Spectramax Plus 384 (Molecular Devices, D) at room temperature for 5 min (Weis et al., J Mol Catal B: Enzym, 2004, 29, 211).

The influence of different $MnCl_2$ concentrations on the quality of the R-HNL random mutagenesis libraries was characterized by assaying in each case 96 transformants per $MnCl_2$ concentration used for activity of converting (R)-2-chloromandelonitrile. The results are summarized in table 1. The largest proportion of active clones was achieved without addition of $MnCl_2$. This condition was chosen in order to produce 10 000 transformants.

TABLE 1

| Comparison of various epPCR conditions | |
|---|---|
| epPCR condition | Proportion of active clones (%) |
| 0 mM $MnCl_2$ | 25-30% |
| 0.05 mM $MnCl_2$ | approx. 20% |
| 0.1 mM $MnCl_2$ | approx. 12% |

Approx. 10 000 transformants with random mutations, introduced by means of error prone PCR by means of HotStarTaq DNA polymerase and based on pGAPZAPaHNL5αL1Q, A111G plasmid DNA, or 1000 saturation mutagenesis transformants (based on the pGAPZAPaHNL5αL1Q, A111G plasmid and containing mutations in positions N110 and G112) were tested for improved conversion of (R)-2-chloromandelonitrile. R-HNL transformants with improved activity with respect to conversion of (R)-2-chloromandelonitrile were selected firstly for rescreening and then for further characterization. For rescreening, the selected transformants were streaked out individually. Of each streaked-out transformant, 4-8 individual colonies were again used for inoculating in each case 400 µl of BM5D medium in 2 ml deep well plates. Culturing and subsequent analysis were carried out in a manner similar to the first round of screening.

B) Analysis of PaHNL5 muteins by means of converting hydroxypivalaldehyde to (R)-hydroxypivalaldehyde cyanohydrin.

Single colonies of transformants were used for inoculating 700 µl of BM7,5D medium (0.4 M potassium phosphate, pH 6.0; 13.4 g/l yeast nitrogen base; 75 g/l D-glucose; 0.4 mg/l biotin; 25 µg/ml zeocin) in 2 ml deep well plates and incubated with shaking at 320 rpm and 28° C., 80% humidity. After an incubation period of 120 hours, the cells were removed by centrifugation and the culture supernatant was used directly for measuring enzyme activity.

The activity assay was carried out in 2 steps. Firstly, hydroxypivalaldehyde was enzymatically converted to the corresponding (R)-hydroxypivalaldehyde cyanohydrin. This was followed either by determining conversion by way of a color reaction of the remaining aldehyde with 4-hydrazino-7-nitrobenzofurazane (NBDH) or by determining the enantiomeric excess after derivatization of the reaction mixture by means of GC on a cyclodextrin column (CP-Chirasil-Dex CB).

R-HNL transformants with improved activity with respect to converting hydroxypivalaldehyde to (R)-hydroxypivalaldehyde cyanohydrin were selected first for rescreening and then for further characterization. For rescreening, the selected transformants were streaked out individually. Of each streaked-out transformant, 4-8 individual colonies were again used for inoculating in each case 700 µl of BM7,5D medium in 2 ml deep well plates. Culturing and subsequent analysis were carried out in a manner similar to the first round of screening.

I) Conversion of Hydroxypivalaldehyde:

The cyanohydrin reaction was carried out in 2 ml Scienceware® 96 deep-well plates (Scienceware/Bel-Art) at room temperature. 400 µl of culture supernatant were introduced into each well and admixed with 150 µl of 3 M citrate-phosphate buffer (pH 2.4). Subsequently, 200 µl of a hydroxypivalaldehyde substrate solution and a magnetic stir bar (Cat. No. VP 734-2, V&P Scientific, CA, USA) were added to each well. The hydroxypivalaldehyde substrate solution was prepared by adding 1.2 ml of briefly heated, liquid hydroxypivalaldehyde to 46.8 ml of 3 M citrate-phosphate buffer (pH 2.4). Finally, 22 µl of a 12 M NaCN solution were added in order to start the reaction. To prevent HCN from escaping, the deep well plates were covered with SILVERseal™ Sealer aluminum foils (Greiner Bio-One GmbH, D, Cat. No. 676090). The microreaction mixtures were mixed using an Alligator Tumble Stirrer and magnetic stir bars (Cat. No. VP 734-2) from V&P Scientific (CA, USA). A mixing frequency of 25 Hz was chosen during the reaction.

After one hour, the reaction was stopped by removing the SILVERseal™ Sealer aluminum foils and by adding 50 µl of a 50% (v/v) sulfuric acid solution. As a result, the pH of the reaction solutions was shifted to pH<1.0, conversion of hydroxypivalaldehyde was stopped, and the HCN cosubstrate was removed in this way. The reaction mixture was subsequently analyzed.

II) Determination of Conversion by Way of a Color Reaction with 4-hydrazino-7-nitrobenzofurazan (NBDH):

This screening method allows the remaining aldehyde concentration in the hydroxypivalaldehyde reaction mixtures to be determined. The FLUOstar OPTIMA plate reader from BMG LABTECH GmbH (Offenburg, D) was used for fluorimetric analysis. The 485-P filter was used as excitation filter and the 520-P filter was used as emission filter. Fluorimetric analysis was carried out in 96 well PP microtiter plates from Greiner Bio-One (Cat. No. 651201). Each well was charged with 150 µl of 3 M citrate-phosphate buffer (pH 2.4) to which 10 µl of the 1:10 diluted hydroxypivalaldehyde reaction mixtures were then added, with finally 60 µl of a saturated NBDH/ethanol solution being added in order to start conversion of NBDH to the corresponding hydrazone. The increase in the highly fluorescent hydrazone was monitored over 3 minutes and the slope of this reaction was directly correlated to the amount of aldehyde remaining in the reaction mixtures.

III) Determination of the Enantiomeric Excess by Means of Chiral GC:

Hydroxypivalaldehyde and the corresponding cyanohydrins formed during enzymatic conversion were extracted with methyl tert-butyl ether (MTBE): the hydroxypivalaldehyde reaction mixtures in the 96 well plates were admixed with 500 µl of MTBE and stirred at 20 Hz for 5 min by means of the Alligator Tumble Stirrer from V&P Scientific (CA, USA). After another 10 min, 35 µl of the organic phase were transferred to 96 well PP microtiter plates from Greiner Bio-One (Cat. No. 651201). Subsequently, 140 µl of $CH_2Cl_2$, 23 µl of acetoanhydride and 23 µl of pyridine were added, and the microtiter plates were sealed with SILVERseal™ Sealer aluminum foils (Greiner Bio-One GmbH, D, Cat. No. 676090). Derivatization was carried out on a Titramax 1000 shaker from Heidolph Instruments (D) at 450 rpm and room temperature for 30 min. The derivatized samples were then analyzed by means of a Hewlett Packard 6890 GC on a cyclodextrin column (CP-Chirasil-Dex CB (25 m×0.32 mm, 0.25 µm film)). A GC PAL, CTC-10022 Autosampler from CTC Analytics was used as autosampler. It was possible to cool the samples at 4° C. during measurements. Further settings for the detector and inlet and the temperature program used and the retention times obtained for R- and S-hydroxypivalaldehyde cyanohydrin are listed below:

Inlet:
  Setting: split
  Gas: $H_2$
  Temperature: 250° C.
  Pressure: 1.0 bar
  Split ratio: 20:1

Temperature Program:
  110° C.-0 min
  10° C./min to 130° C.
  20° C./min to 170° C.
  170° C.-0.5 min
  Time: 4.5 min FID Detector:
  Temperature: 250° C.
  $H_2$: 20 ml/min
  Air: 200 ml/min
  $N_2$: 30 ml/min Retention Times:
  R-Hydroxypivalaldehyde cyanohydrin: 2.44 min
  S—Hydroxypivalaldehyde cyanohydrin: 2.55 min

EXAMPLE 4

Sequence Check by Means of "Colony PCR"

The best *Pichia* transformants were characterized by amplifying and sequencing the integrated, mutated hnl5 gene by means of PCR.

For this purpose, a *Pichia pastoris* single colony was resuspended in 50 µl of Y-Per® and heated to 65° C. for 10 min. The mixture was cooled briefly on ice, then admixed with 60 µl of phenol/chloroform/isoamyl alcohol (25/24/1) and mixed well. This reaction mixture was centrifuged at 13 200 rpm in a bench centrifuge for 30 min. After centrifugation the aqueous phase was transferred to a fresh Eppendorf tube and purified by means of ethanol precipitation. The precipitated DNA was then dissolved in 50 µl of water (purest quality), and 2-5 µl of this DNA preparation were used as template for PCR amplification of the mutated hnl5 gene. The reaction mixture with a total volume of 100 µl moreover included the two primers, pGAPZA484f and HNL5alp21, with a concentration of in each case 0.4 µM, 0.2 mM dNTPs, 1× Phusion HF buffer and 1.2 U of Phusion High-Fidelity DNA Polymerase from Finnzymes (Cat. No. F530L). The 3-stage PCR was carried out in an Applied Biosystems thermocycler and comprised the following steps:

30 s at 98° C., followed by 35 cycles of in each case 10 s at 98° C., 20 s at 60° C. and 1 min at 72° C., and finally a single incubation of 7 min at 72° C.

After two purifications by means of the QIAquick PCR Purification Kit from Qiagen (Cat. No. 28106), the PCR product was used for sequencing.

```
Primer sequences:
HNL5alp21:
                                        (SEQ ID NO: 19)
5'-ATGGTACCGAATTCTCACATGGACTCTTGAATATTATGAATAG-3' pGAPZA484f:
                                        (SEQ ID NO: 7)
5'-TTCGAAACGAGGAATTCACGATGAG-3'
```

The integrated hn15 genes of the random mutagenesis R-HNL transformants with improved activity of converting (R)-2-chloromandelonitrile and, respectively, hydroxypivalaldehyde, were checked by amplification and sequencing according to the colony PCR method.

EXAMPLE 5

Recloning of Isolated Variants of the PahnI5 Gene into the pHILD2 Vector and Cultivation of *Pichia pastoris* pHILD2 Transformants To confirm that the randomly generated mutations in the PahnI5 gene have contributed to improving the corresponding PahnI5 genes, to purify "multicopy transformants" and to improve expression, the integrated mutated hnI5 gene was amplified by means of PCR, cloned by means of EcoRI cleavage sites into the pHILD2 vector (Invitrogen, San Diego, Calif.) and checked for correct orientation. Amplification of the integrated mutated PahnI5 genes from genomic DNA of the *Pichia pastoris* transformants was described in example The best *Pichia* transformants were characterized by amplifying again and sequencing the integrated, mutated hnI5 gene by means of PCR. This was carried out in a manner similar to example 4.

Table 2 depicts an overview of the particular expression strains of the best mutants:

TABLE 2

| | | Changes introduced into the Pahnl5 gene | | |
|---|---|---|---|---|
| Method of preparation | PaHNL5 mutein name | *Pichia* clone name | Amino acid substitution | Change in DNA sequence |
| Random mutagenesis based on the pGAPZAPaHNL5αL1Q, A111G plasmid | 1_H10 | GS115 pHILD2-PaHNL5αL1Q, I304V, A111G, 1_H10 | A111G I304V | GCA → GGA ATT → GTT |
| | 4_E10 | GS115 pHILD2-PaHNL5αL1Q, A111G, 4_E10 | A111G silent mutation in position 85 and position 432 | GCA → GGA CCA → CCG TAT → TAC |
| | 2_A11* | GS115 pHILD2-PaHNL5αL1Q, I108M, A111G, 2_A11* | I108M A111G | ATA → ATG GCA → GGA |
| | 16_A3 | GS115 pHILD2-PaHNL5αL1Q, N110S, A111G, 16_A3 | N110S A111G | AAT → AGT GCA → GGA |
| | 16_E10 | GS115 pHILD2-PaHNL5αL1Q, I108M, A111G, 16_E10 | I108M A111G silent mutation in position 278 | ATA → ATG GCA → GGA CTA → TTA |
| | 25_A6 | GS115 pHILD2-PaHNL5αL1Q, N110S, A111G, 25_A6 | N110S A111G silent mutation in position 209 | AAT → AGT GCA → GGA TTG → CTG |
| | 25_H2 | GS115 pHILD2-PaHNL5αL1Q, N3I, A111G, 25_H2 | N3I A111G | AAT → ATT GCA → GGA |
| | 27_G11 | GS115 pHILD2-PaHNL5αL1Q, I108M, A111G, Y432F, V424A, 27_G11 | I108M A111G Y432F V424A | ATA → ATG GCA → GGA TAT → TTT GTG → GCG |
| | 40_B8 | GS115 pHILD2-PaHNL5αL1Q, I304V, A111G, 40_B8 | A111G I304V | GCA → GGA ATT → GTT |
| Saturation mutagenesis based on the pGAPPamHNL5a plasmid | N2A | GS115 pHILD2-PaHNL5αV317A | V317A | GTA → GCT |
| Saturation mutagenesis based on the pGAPZAPaHNL5αL1Q, A111Gplasmid | N110X-G112X | GS115 pHILD2-PaHNL5αL1Q, N110S, A111G | N110S A111G | AAT → AGT GCA → GGA |

4. The two primers used, HNL5alp21 and pGAPZA484f, comprised EcoRI cleavage sites.

The resulting plasmids were transformed into *Pichia pastoris* GS115 according to the Invitrogen standard protocol. In each case approx. 100 transformants were transferred to deep well culture plates for inoculation, using sterile toothpicks, and cultivated for screening for active transformants.

To this end, 250 µl of BM0,5G medium (0.2 M potassium phosphate, pH 6.0; 13.4 g/l yeast nitrogen base; 5 g/l glycerol; 0.4 mg/l biotin) in 2 ml deep well plates were inoculated with single colonies of transformants and incubated with shaking at 320 rpm and 28° C., 80% humidity. Expression via the AOX1 promoter was induced by adding 250 µl of BMM2 medium (0.2 M potassium phosphate, pH 6.0; 13.4 g/l yeast nitrogen base; 10 ml/1 methanol; 0.4 mg/l biotin) after 60-70 hours. After a further 10, 24 and 48 hours, more methanol was added by way of adding in each case 50 µl of BMM10 medium (0.2 M potassium phosphate, pH 6.0; 13.4 g/l yeast nitrogen base; 50 ml/1 methanol; 0.4 mg/l biotin). Approx. 72 hours after the first MeOH induction, the cells were removed by centrifugation and the culture supernatant was directly used for measuring enzyme activity.

EXAMPLE 6

Cultivation of *Pichia pastoris* R-HNL Mutants of the First Round of Random Mutagenesis in 2 l Shaker Flasks and Characterization of PaHNL5 Muteins Using (R)-2-chloromandelonitrile and 2-chlorobenzaldehyde A) Cultivation of Recloned R-HNL Transformants in 2 l Shaker Flasks Precultures comprising 50 ml of YPD medium (10 g/l Bacto™ yeast extract, 20 g/l Bacto™ peptone, 20 g/l D-glucose) were inoculated with large single colonies and incubated with shaking at 120 rpm and 28° C., 80% humidity, overnight. Subsequently, 225 ml of BM0,5G medium (0.2 M potassium phosphate, pH 6.0; 13.4 g/l yeast nitrogen base; 5 g/l glycerol; 0.4 mg/l biotin) in 2 l flasks with baffles were inoculated with the precultures to give a starting OD of 0.05 and incubated with shaking at 120 rpm and 28° C., 80% humidity. Expression via the AOX1 promoter was induced by adding 25 ml of BMM10 medium (0.2 M potassium phosphate, pH 6.0; 13.4 g/l yeast nitrogen base; 50 ml/l methanol; 0.4 mg/l biotin) after 60-70 hours. Further methanol additions of 2.5 ml per shaker flask (250 ml) were carried out after 10, 24 and 48 hours.

Approx. 72 hours after the first methanol induction, the cells were removed by centrifugation and the culture supernatant was used directly, or in diluted or concentrated form for measuring enzyme activity.

B) Characterization of PaHNL5 Variants

To determine the specific activity of the particular mutants, the expression clones were cultured in each case in a plurality of shaker flasks. The culture supernatant was concentrated by ultrafiltration (10 kDa cutoff) using 20 ml Vivaspin PES centrifugation columns from Sartorius (Göttingen, D). Protein concentration was subsequently carried out using a Biorad (Hercules, Calif.) protein assay (Bradford). The standard used for producing a calibration line was native PaHNL from Sigma (M-6782 Lot 41H4016).

Samples containing approx. 3 µg of total protein were taken from the enzyme samples and applied directly to a gel (protein gel NuPAGE 4-12% Bis Gel 1.0 mm×15 well; Invitrogen). Furthermore, samples containing approx. 1.5 µg of total protein were deglycosylated by endoglycosidase H (Cat. #P0702L, NEB) according to the protocol provided by the supplier and then applied. The standard used was SeeBlue Plus2 Pre-Stained Standard from Invitrogen (Carlsbad, USA).

C) Cleavage of (R)-2-chloromandelonitrile:

Firstly, the enzyme activities of the mutants of the invention with regard to cleavage of the substrate (R)-2-chloromandelonitrile (DSM Fine Chemicals Linz, A) were determined photometrically. To this end, 0.7 µl of 0.1 M phosphate-citrate buffer (pH 5.0) were introduced to quartz cuvettes and admixed with 100 µl of a suitably diluted enzyme solution. The reaction was started by finally adding 200 µl of an (R)-2-chloromandelonitrile substrate solution (10 mg/ml (R)-2-chloromandelonitrile in 0.1 M phosphate-citrate buffer (pH 3.5)). The slope of the absorbance profile at 300 nm was monitored for 5 min. The specific activities of the R-HNL muteins of the first random mutagenesis library are summarized in table 3.

TABLE 3

Specific activities of PaHNL5αL1Q, PaHNL5αL1Q, A111G (WO 2004/083424) and the mutants of the invention with regard to cleavage of the substrate (R)-2-chloromandelonitrile

| Pichia clone name | Name of R-HNL variant | Specific activity of (R)-2-chloromandelonitrile cleavage [U/mg] |
|---|---|---|
| GS115 pHILDPaHNL5αL1Q | WT | 2.464 +/− 0.227 |
| GS115 pHILDPaHNL5αL1Q, A111G | A111G | 15.03 +/− 1.16 |
| GS115 pHILD2-PaHNL5αL1Q, A111G, 4_E10 | A111G4_E10 | 20.12 +/− 0.52 |
| GS115 pHILD2-PaHNL5αL1Q, N3I, A111G, 25_H2 | N3IA111G | 17.23 +/− 1.68 |
| GS115 pHILD2-PaHNL5αL1Q, I108M, A111G, 2_A11* | I108MA111G | 29.16 +/− 1.68 |
| GS115 pHILD2-PaHNL5αL1Q, I304V, A111G, 40_B8 | I304VA111G | 15.24 +/− 1.56 |
| GS115 pHILD2-PaHNL5αL1Q, N110S, A111G, 16_A3 | N110SA111G | 72.93 +/− 1.98 |

The muteins A111G4_E10, N3IA111G, I108MA111G and N110SA111G showed improved specific activity of (R)-2-chloromandelonitrile cleavage.

I304VA111G showed high activity directly in the culture supernatant but no improved specific activity, suggesting increased expression.

D) Synthesis of (R)-2-chloromandelonitrile

To compare the selectivities of the mutants of the invention for (R)-2-chloromandelonitrile synthesis, 15 mmol of 2-chlorobenzaldehyde were dissolved in 2.1 ml of tert-butyl methyl ether (MTBE). The corresponding PaHNL preparation (0.5 mg) was diluted with 50 mM phosphate-citrate buffer (pH 3.4) to give a final volume of 3.7 ml. The buffered solution was again adjusted to pH 3.4 and then mixed with the substrate dissolved in MTBE in 30 ml glass vials. The solution was cooled to 10° C., and 1.2 ml of liquid HCN were metered in using a syringe. A Variomag Electronicrührer Poly 15 magnetic stirrer from H+P Labortechnik (Oberschleißheim, D) was used for stirring at 700 rpm to produce an emulsion.

Samples were taken at various points in time, derivatized with acetic anhydride in the presence of pyridine and dichloromethane and analyzed by means of GC on a cyclodextrin column (CP-Chirasil-Dex CB).

Table 4 depicts the results for conversion (% conv) and enantiomeric excess (% ee) of the R-HNL variants of the invention after different points in time.

TABLE 4

Conversion and enantiomeric excess of PaHNL5αL1Q, PaHNL5αL1Q, A111G (both of WO 2004/083424) and the R-HNL variants of the invention with regard to (R)-2-chloromandelonitrile synthesis (n.d.—not determined)

| | Reaction time | | | | | | | |
|---|---|---|---|---|---|---|---|---|
| | 1 h | | 2 h | | 4 h | | 6 h | |
| PaHNL variant (0.5 mg) | Conv (%) | ee (%) | Conv (%) | ee (%) | Conv (%) | ee (%) | Conv (%) | ee (%) |
| WT | 21.2 | n.d. | 33.5 | n.d. | 51.8 | n.d. | 64.3 | n.d. |
| A111G | 52.5 | n.d. | 68.6 | n.d. | 83.6 | n.d. | 90.8 | n.d. |
| A111G4_E10 | 61.3 | 98.9 | 72.9 | 98.8 | 86.3 | 98.7 | 92.0 | 98.7 |
| N3IA111G | 56.7 | 98.8 | 72.8 | 98.8 | 87.0 | 98.6 | 93.3 | 98.7 |
| I108MA111G | 75.9 | 99.4 | 86.3 | 99.4 | 95.03 | 99.4 | 97.8 | 99.4 |
| N110SA111G | 18.7 | 96.7 | 31.0 | 95.9 | 47.4 | 94.9 | 59.1 | 94.2 |
| I304VA111G | 53.3 | 98.6 | 70.1 | 98.4 | 85.1 | 98.5 | 92.1 | 98.7 |

The variants A111G4_E10, N3IA111G and I108MA111G produced increased conversion compared to PaHNL5αL1Q, A111G and showed improved activity of (R)-2-chloromandelonitrile synthesis. N110SA111G had reduced activity with regard to (R)-2-chloromandelonitrile synthesis but improved activity with regard to (R)-2-chloromandelonitrile cleavage. This comparison indicates that the N110S mutation results only in an increased catalytic rate of the cleavage reaction.

EXAMPLE 7

Site-Specific Mutagenesis for Combining Advantageous Mutations

In each case 10 ng of the expression plasmids pHILD2-PaHNL5αL1Q, I108M, A111G, 2_A11*; pHILD2-PaHNL5αL1Q, A111G, 4_E10; pHILD2-PaHNL5αL1Q, N110S, A111G, 16_A3 or pHILD2-PaHNL5αV317A (see example 5) were used as template for the mutagenesis reaction by means of the QuikChange XL Site Directed Mutagenesis Kit from Stratagene (Cat. #200516). In each case 200 ng of the particular two mutagenesis primers were used for the reaction.

The following temperature program was used:
A) Denaturation at 95° C. for 1 min
B) 8 cycles, each of 50 s at 95° C., 50 s at 60° C. and 10 min at 68° C.
C) Extension at 68° C. for 7 min.

The template DNA was removed by DpnI digestion as described in the kit's protocol, and 2 μl of the reaction mixture were used as described for transforming ultracompetent *E. coli* XL10 Gold cells. Plasmid DNA was prepared from the transformants and sequenced. Plasmids of mutants having the correct sequence in the region of the coding DNA insert were amplified and transformed into *Pichia pastoris* GS115 with the aid of the Invitrogen standard protocol.

Approx. 100 histidine-autotrophic *Pichia* transformants were cultured in deep well plates, and the activity of the culture supernatants was tested by means of the (R)-2-chloromandelonitrile cleavage reaction (see example 3). In each case clones having the highest enzyme activity among the individual mutants were selected for shaker flask experiments.

PCR-Primers for Site-Specific Mutagenesis:
For the N3I mutation, based on the pHILD2-PaHNL5αL1Q, I108M, A111G, 2A11* plasmid or the pHILD2-PaHNL5αL1Q, I108M, A111G, 4E_10 plasmid:

```
                                       (SEQ ID NO: 20)
N3If:    5'-GCTGAAGCTCAAGCCATTACTTCTGCTCATGAT-3'

(SEQ ID NO: 21)
N3Ir:    5'-ATCATGAGCAGAAGTAATGGCTTGAGCTTCAGC-3'
```

For the I108M mutation, based on the pHILD2-PaHNL5αL1Q, N110S, A111G, 16 A3 plasmid:

```
                                       (SEQ ID NO: 22)
I108Mf:  5'-CTCGGTGGCACGACCATGATCAGTGGAGGCGTC-3'

(SEQ ID NO: 23)
I108Mr:  5'-GACGCCTCCACTGATCATGGTCGTGCCACCGAG-3'
```

For the I108M mutation, based on the pHILD2-PaHNL5αL1Q, A111G, 4 E10 plasmid:

```
                                       (SEQ ID NO: 24)
I108M2f: 5'-CTCGGTGGCACGACCATGATCAATGGAGGCGTC-3'

(SEQ ID NO: 25)
I108M2r: 5'-GACGCCTCCATTGATCATGGTCGTGCCACCGAG-3'
```

For the N225S mutation, based on the pHILD2-PaHNL5αL1Q, I108M, A111G, 2 A11* plasmid:

```
                                       (SEQ ID NO: 26)
N225Sf:  5'-GAAGATCCTCTTCTCTTCCTCTACATCAAATTTGTCAGC
         TATTG-3'

(SEQ ID NO: 27)
N225Sr:  5'-CAATAGCTGACAAATTTGATGTAGAGGAAGAGAAGAGGA
         TCTTC-3'
```

For the I108M and A111G mutations, based on the pHILD2-PaHNL5αV317A plasmid:

```
                                       (SEQ ID NO: 24)
I108M2f: 5'-CTCGGTGGCACGACCATGATCAATGGAGGCGTC-3'

(SEQ ID NO: 25)
I108M2r: 5'-GACGCCTCCATTGATCATGGTCGTGCCACCGAG-3'
```

The PaHNL combination variants prepared in this way were thus: I108MA111G4_E10, N3II108MA111G, N3II108MA111G4_E10, I108MN110SA111G, I108MA111GN225S and I108MA111GV317A.

EXAMPLE 8

Production and Characterization of PaHNL5 Enzyme Variants for Conversion of 2-chlorobenzaldehyde To determine the specific activity of the particular mutants, each of the expression clones described in example 7 was cultured in a plurality of 2 l shaker flasks. Cultivation was carried out in a manner similar to example 6A.

The culture supernatant was concentrated by ultrafiltration (10 kDa cutoff) using 20 ml Vivaspin PES centrifugation columns from Sartorius (Göttingen, D) and then used for determining enzyme activity.

To determine substrate specificities, the protein concentration of the enzyme preparations was measured using the Biorad protein assay (Hercules, Ca). Conversion and enantiomeric excess with regard to (R)-2-chloromandelonitrile synthesis were determined by means of GC:

For this purpose, 15 mmol of 2-chlorobenzaldehyde were dissolved in 2.1 ml of methyl tert-butyl ether (MTBE). 0.5 mg of the corresponding PaHNL preparation was diluted with 50 mM phosphate-citrate buffer (pH 3.4) to give a final volume of 3.7 ml. The buffered solution was again adjusted to pH 3.4 and then mixed with the substrate dissolved in MTBE in 30 ml glass vials. The solution was cooled to 10° C., and 1.2 ml of liquid HCN were metered in using a syringe. A Variomag Electronicrührer Poly 15 magnetic stirrer from H+P Labortechnik (Oberschleißheim, D) was used for stirring at 700 rpm to produce an emulsion.

Samples were taken at various points in time, derivatized with acetic anhydride in the presence of pyridine and dichloromethane and analyzed by means of GC on a cyclodextrin column (CP-Chirasil-Dex CB).

Table 5 depicts the results for conversion (% conv) and enantiomeric excess (% ee) of the R-HNL variants of the invention after different points in time.

TABLE 5

Conversion and enantiomeric excess of PaHNL5αL1Q, A111G (WO 2004/083424) and the R-HNL variants of the invention with regard to (R)-2-chloromandelonitrile synthesis

| | Reaction time | | | | | | | |
|---|---|---|---|---|---|---|---|---|
| | 1 h | | 2 h | | 4 h | | 6 h | |
| PaHNL variant (0.5 mg) | Conv (%) | ee (%) | Conv (%) | ee (%) | Conv (%) | ee (%) | Conv (%) | ee (%) |
| A111G | 52.4 | 96.4 | 70.3 | 96.1 | 84.3 | 95.9 | 90.4 | 95.8 |
| I108MA111G | 76.9 | 98.6 | 90.2 | 98.5 | 97.2 | 98.5 | 98.97 | 98.4 |

TABLE 5-continued

Conversion and enantiomeric excess of PaHNL5αL1Q, A111G
(WO 2004/083424) and the R-HNL variants of the invention with regard to
(R)-2-chloromandelonitrile synthesis

| | Reaction time | | | | | | | |
|---|---|---|---|---|---|---|---|---|
| | 1 h | | 2 h | | 4 h | | 6 h | |
| PaHNL variant (0.5 mg) | Conv (%) | ee (%) | Conv (%) | ee (%) | Conv (%) | ee (%) | Conv (%) | ee (%) |
| I108MA111GN225S | 77.9 | 98.5 | 90.3 | 98.4 | 97.3 | 98.4 | 98.9 | 98.3 |
| I108MA111GV317A | 64.7 | 98.2 | 83.1 | 98.2 | 94.6 | 98.2 | 97.8 | 98.3 |
| I108MA111G4_E10 | 79.8 | 98.87 | 91.4 | 98.8 | 98.2 | 98.8 | 99.4 | 98.8 |
| N3II108MA111G | 80.6 | 98.9 | 92.3 | 98.8 | 98.1 | 98.9 | 99.5 | 98.9 |
| N3II108MA111G4_E10 | 83.5 | 98.7 | 94.6 | 98.6 | 98.6 | 98.7 | 99.7 | 98.6 |
| I108MN110SA111G | 31.8 | 98.2 | 49.0 | 97.5 | 67.4 | 97.2 | 77.3 | 96.8 |

The combination of I108MA111G with N225S showed no further improvement in conversion or enantiomeric excess. However, by combining the best mutations of the first random mutagenesis library, it was possible to further increase conversion compared to the I108MA111G variant. Virtually complete conversion was achieved already after 6 hours, using only 33.3 mg of unpurified enzyme preparation per mole of substrate. The N3I108MA111G4_E10 variant, for example, achieved a conversion of 99.7% after 6 h.

EXAMPLE 9

Production of A111G (WO 2004/083424),
A111G4_E10, N3IA111G, I108MA111G,
N3II108MA111G and N3II108MA111G4_E10
Muteins in a 5 l Bioreactor A sufficient amount of enzyme of the clones *Pichia pastoris* GS115 pHILDPaHNL5alphaL1Q, A111G of WO 2004/083424, and the clones described in examples 6-8, *Pichia pastoris* GS115 pHILD2-PaHNL5αL1Q, A111G, 4_E10; *Pichia pastoris* GS115 pHILD2-PaHNL5αL1Q, N3I, A111G, 25_H2; *Pichia pastoris* GS115 pHILD2-PaHNL5αL1Q, I108M, A111G, 25_A11*; *Pichia pastoris* GS115 pHILD2-PaHNL5αL1Q, N3I, I108M, A111G and *Pichia pastoris* GS115 pHILD2-PaHNL5αL1Q, N3I, I108M, A111G4_E10, was produced in a 5 l fermenter for further characterizations. Mut$^s$ strains were chosen for culturing.

First, a preculture of each clone comprising 50 ml of YPD medium (10 g/l Bacto™ yeast extract, 20 g/l Bacto™ peptone, 20 g/l D-glucose) was inoculated with a large single colony and incubated at 28° C. and 120 rpm for 24 h. The first preculture was used to inoculate 2×200 ml YPD medium in 2 l flasks with baffles. Incubation was carried out for approx. 20 h at 28° C. and 120 rpm.

Chemicals 1-7, amounts calculated for 3.5 liters, were dissolved in deionized water and introduced into a 5 l bioreactor (Biostat®CT from Sartorius, Göttingen, D). After in situ sterilization, the pH of the medium was adjusted to pH 5.0 with 25% ammonia by way of sterile addition through a feed pump. This was followed by introducing into the bioreactor 13.5 ml of sterile-filtered trace element solution comprising vitamin H by means of a sterile syringe.

Approx. 400 ml of preculture from in each case two 2 l shaker flasks were used for inoculation. The starting $OD_{600}$ in the fermenter was 1-2. With an operating temperature of 28° C., an aeration rate of 2.5-10 liters of air/min and a stirring speed between 500 and 1500 rpm, the partial pressure of oxygen ($pO_2$) was maintained at a value >30% of the saturation concentration. The pH of the culture medium was kept constant at pH 5.0 by sterile addition of 25% ammonia through a feed pump.

After the initially introduced glycerol had been consumed, after a fermentation time of 15-20 hours, metering-in of the glycerol medium was started, initially at 45 ml/h. The metering-in rate was increased in steps to 90-100 ml/h and continued for approx. 12 hours, until approx. 150 $OD_{600}$ were reached. Metering-in of glycerol was then stopped.

The third phase of fermentation was initiated by inducing expression by metering in methanol. The metering-in rate was adjusted initially to 10-15 ml/h. This rate was increased in steps to 45-60 ml/h over 12-15 hours and maintained for another 60 hours.

After approx. 72 hours of methanol induction, the cells were harvested by two centrifugations at 4000 rpm in a Beckman Coulter™ (Fullerton, Calif., USA) Avanti™ J-20XP centrifuge with the Beckman JLA 8.1000 rotor at 4° C. for 20 min. The culture supernatant was collected and the enzyme activity of (R)-2-chloromandelonitrile cleavage was determined. The fermentation supernatant was diluted appropriately with 0.1 M phosphate-citrate buffer (pH 5.0) and, after addition of the (R)-2-chloromandelonitrile substrate solution (10 mg/ml (R)-2-chloromandelonitrile in 0.1M phosphate-citrate buffer (pH 3.5)), the absorbance profile at 300 nm was monitored in microtiter plates for 5 min. Enzyme activity in the culture supernatant after centrifugation was approx. 10-15 times greater than after fermentation in 2 l shaker flasks.

The culture supernatant was concentrated by means of crossflow ultrafiltration using 30 kDa cutoff modules from Sartorius (VIVASCIENCE Vivaflow 50 from Sartorius, Göttingen, D). Thus enzyme preparations with a protein concentration of 1-3 mg/ml were produced which were stored at 4° C. for a short time and at −20° C. for a longer period. Since *Pichia pastoris* secretes hardly any of its own proteins into the culture supernatant, the enzyme produced and concentrated in this way was already very pure.

The following chemicals were utilized for preparing the culture medium (amount per 3.5 l):

| | | |
|---|---|---|
| 1. | 85% ortho-phosphoric acid | 73.5 ml |
| 2. | $CaSO_4 \cdot 2H_2O$ | 3.15 g |
| 3. | $K_2SO_4$ | 50.05 g |
| 4. | $MgSO_4 \cdot 7H_2O$ | 42.7 g |
| 5. | KOH | 11.55 g |
| 6. | Glycerol | 140 g |
| 7. | Deionized water, conductivity: 5.5-9.1 μS/cm | 3.5 l |
| 8. | Antifoam: 10% Acepol 83E (Carl Becker Chemie GmbH, Hamburg, D) | 1 ml |
| 9. | 4.35 ml/l trace element solution (addition after in situ sterilization) | |

-continued

| | | |
|---|---|---|
| 10. 25% ammonia, technical grade | | |
| Trace element solution with vitamin H (amount per l): | | |
| 11. Biotin | 0.2 | g |
| 12. $CuSO_4 \cdot 5H_2O$ | 6.0 | g |
| 13. KI | 0.09 | g |
| 14. $MnSO_4 \cdot H_2O$ | 3.0 | g |
| 15. $Na_2MoO_4 \cdot 2H_2O$ | 0.2 | g |
| 16. $H_3BO_3$ | 0.02 | g |
| 17. $CoCl_2$ | 0.5 | g |
| 18. $ZnSO_4 \cdot 7H_2O$ | 42.2 | g |
| 19. $Fe(II)SO_4 \cdot 7H_2O$ | 65 | g |
| 20. $H_2SO_4$ | 5 | ml |

Glycerol Medium:

750 g of glycerol were admixed with deionized water to give 1.5 l, dissolved and sterilized. Subsequently, 12 ml/l trace element solution were added.

Methanol Medium:

0.9 l of methanol were introduced to a sterile 2 l bottle and admixed with 12 ml/l trace element solution.

EXAMPLE 10

Purification and Characterization of the Enzyme Variants Produced in the 5 l Fermenter The enzyme preparations produced in the fermenter and then concentrated were chromatographically purified.

Prior to purification, the concentrated enzyme preparations were equilibrated by repeatedly diluting and concentrating with the low-salt binding buffer A (20 mM citrate-phosphate buffer, pH 5.5). This is carried out by crossflow ultrafiltration by means of 30 kDa cutoff modules (VIVASCIENCE Vivaflow 50 from Sartorius, Göttingen, D). The equilibrated enzyme preparations were then purified on an ÄKTApurifier 10 FPLC instrument from Amersham Biosciences UK Limited (Buckinghamshire, UK) via an anion exchanger Q-Sepharose Fast Flow (QFF) column with a column volume of 10 ml. Elution was carried out using elution buffer B (20 mM citrate-phosphate buffer+1M NaCl, pH 5.5). Prior to purification, the column was equilibrated with five column volumes of buffer A. Thereafter, the gradient profile listed in table 6 was used for the various PaHNL5 variants from heterologous production by *Pichia pastoris*:

TABLE 6

Gradient profile for purifying various PaHNL5 variants by means of 10 ml anion exchanger Q-Sepharose Fast Flow (QFF) column:

| Step | Buffer B | Volume (in column volumes) |
|---|---|---|
| Washing without fractionation | 0% | 1 |
| Gradient 1 | 0-4% | 0.5 |
| Gradient 2 | 4-48% | 1 |
| Gradient 3 | 48-60% | 0.5 |
| Gradient 4 | 60-100% | 1 |
| Washing without fractionation | 100% | 1.5 |

A flow rate of 2 ml/min and a fraction volume of 2 ml were chosen. The protein content of those fractions which, according to evaluation of the chromatogram, should contain protein (depending on peak position), was measured by means of Biorad (Hercules, Calif.) protein assay (Bradford method). The enzyme activity of cleaving (R)-2-chloromandelonitrile was also determined in these fractions. The 2-3 fractions containing the highest activity were pooled and used for further analysis of enzyme characteristics. The protein concentration was determined by means of Biorad (Hercules, Calif.) protein assay (Bradford). The standard used for preparing the calibration lines was native PaHNL from Sigma (M-6782 Lot 41H4016).

Samples containing approx. 3 µg of total protein were taken from the enzyme samples and applied directly to a gel (protein gel NuPAGE 4-12% Bis Gel 1.0 mm×15 well; Invitrogen). Furthermore, samples containing approx. 1.5 µg of total protein were deglycosylated by endoglycosidase H (Cat. #P0702L, NEB) according to the protocol provided by the supplier and then applied to a protein gel. The standard used was SeeBlue Plus2 Pre-Stained Standard from Invitrogen (Carlsbad, USA).

The enzyme properties were determined by using the purified R-HNL variants for the synthesis of (R)-2-chloromandelonitrile, (R)-2-bromomandelonitrile and (R)-2-fluoromandelonitrile, respectively.

For this purpose, 15 mmol of 2-chlorobenzaldehyde, 2-bromobenzaldehyde, or 2-fluorobenzaldehyde were dissolved in 2.1 ml of methyl tert-butyl ether (MTBE). The appropriate PaHNL variant (0.25 mg or 0.5 mg) was diluted with 50 mM phosphate-citrate buffer (pH 3.4) to give a final volume of 3.7 ml. The buffered solution was again adjusted to pH 3.4 and then mixed with the substrate dissolved in MTBE in 30 ml glass vials. The solution was cooled to 10° C., and 1.2 ml of liquid HCN were metered in using a syringe. A Variomag Electronicrührer Poly 15 magnetic stirrer from H+P Labortechnik (Oberschleißheim, D) was used for stirring at 700 rpm to produce an emulsion.

Samples were taken at various points in time, derivatized with acetic anhydride in the presence of pyridine and dichloromethane and analyzed by means of GC on a cyclodextrin column (CP-Chirasil-Dex CB).

Table 7 a)-d) depicts the results for conversion (% conv) and enantiomeric excess (% ee) of the R-HNL variants of the invention after different points in time.

TABLE 7a

Conversion and enantiomeric excess of purified R-HNL variants after production in a 5 l fermenter: the variants PaHNL5αL1Q, A111G (WO 2004/083424) and the R-HNL variants of the invention were used for synthesis of (R)-2-chloro-mandelonitrile.

| | Reaction time | | | | | | | |
|---|---|---|---|---|---|---|---|---|
| | 0.5 h | | 1 h | | 2 h | | 4 h | |
| PaHNL variant (0.5 mg) | Conv (%) | ee (%) | Conv (%) | ee (%) | Conv (%) | ee (%) | Conv (%) | ee (%) |
| A111G | 45.2 | 98.4 | 64.8 | 98.1 | 79.2 | 98.0 | 90.6 | 97.9 |
| I108MA111G | 72.2 | 99.3 | 88.6 | 99.3 | 95.2 | 99.3 | 98.2 | 99.2 |
| A111G4_E10 | 68.5 | 99.3 | 85.7 | 99.3 | 94.0 | 99.2 | 98.5 | 99.2 |

TABLE 7a-continued

Conversion and enantiomeric excess of purified R-HNL variants after production in a 5 l fermenter: the variants PaHNL5αL1Q, A111G (WO 2004/083424) and the R-HNL variants of the invention were used for synthesis of (R)-2-chloro-mandelonitrile.

| | \multicolumn{8}{c}{Reaction time} | | | | | | | |
|---|---|---|---|---|---|---|---|---|
| | 0.5 h | | 1 h | | 2 h | | 4 h | |
| PaHNL variant (0.5 mg) | Conv (%) | ee (%) | Conv (%) | ee (%) | Conv (%) | ee (%) | Conv (%) | ee (%) |
| N3IA111G | 62.8 | 99.2 | 81.5 | 99.0 | 91.3 | 99.0 | 97.4 | 99.0 |
| N3II108MA111G | 73.3 | 99.4 | 89.0 | 99.4 | 95.9 | 99.5 | 99.1 | 99.4 |
| N3II108MA111G4_E10 | 74.6 | 99.5 | 90.7 | 99.5 | 96.3 | 99.5 | 99.1 | 99.4 |

TABLE 7b

Conversion and enantiomeric excess of purified R-HNL variants after production in a 5 l fermenter: the variants PaHNL5αL1Q, A111G (WO 2004/083424) and the R-HNL variants of the invention were used for synthesis of (R)-2-bromo-mandelonitrile.

| | Reaction time | | | | | |
|---|---|---|---|---|---|---|
| | 1 h | | 2 h | | 4 h | |
| PaHNL variant (0.5 mg) | Conv (%) | ee (%) | Conv (%) | ee (%) | Conv (%) | ee (%) |
| A111G | 26.27 | 97.34 | 40.74 | 97.83 | 60.51 | 98.11 |
| I108MA111G | 51.08 | 98.95 | 68.53 | 99.17 | 82.17 | 99.30 |
| N3II108MA111G4_E10 | 23.71 | 96.97 | 36.82 | 97.61 | 55.06 | 97.68 |

TABLE 7c

Conversion and enantiomeric excess of purified R-HNL variants after production in a 5 l fermenter: the variants PaHNL5αL1Q, A111G (WO 2004/083424) and the R-HNL variants of the invention were used for synthesis of (R)-2-fluoro-mandelonitrile.

| | Reaction time | | | | | |
|---|---|---|---|---|---|---|
| | 1 h | | 2 h | | 4 h | |
| PaHNL variant (0.5 mg) | Conv (%) | ee (%) | Conv (%) | ee (%) | Conv (%) | ee (%) |
| A111G | 97.57 | 99.71 | 99.55 | 99.81 | 99.94 | 99.84 |
| I108MA111G | 99.68 | 99.89 | 99.84 | 99.95 | 99.92 | 99.92 |
| N3II108MA111G4_E10 | 96.33 | 99.82 | 99.21 | 99.83 | 99.85 | 99.82 |

TABLE 7d

Conversion and enantiomeric excess of unpurified R-HNL variants after production in a 5 l fermenter: in each case 0.25 mg of the variants PaHNL5αL1Q, A111G (WO 2004/083424) and the R-HNL variants of the invention were used for synthesis of (R)-2-chloromandelonitrile.

| | Reaction time | | | | | | | |
|---|---|---|---|---|---|---|---|---|
| | 0.5 h | | 1 h | | 2 h | | 4 h | |
| PaHNL variant (0.25 mg) | Conv (%) | ee (%) | Conv (%) | ee (%) | Conv (%) | ee (%) | Conv (%) | ee (%) |
| A111G | 15.1 | 95.2 | 31.3 | 95.3 | 38.3 | 95.1 | 52.5 | 95.4 |
| I108MA111G | 36.3 | 98.8 | 57.4 | 98.5 | 70.6 | 98.4 | 81.4 | 98.2 |
| A111G4_E10 | 34.4 | 98.5 | 54.9 | 98.3 | 68.9 | 98.1 | 81.6 | 98.1 |
| N3IA111G | 33.8 | 98.4 | 54.1 | 98.2 | 68.6 | 98.2 | 80.6 | 98.1 |
| N3II108MA111G | 40.4 | 98.6 | 60.8 | 98.5 | 73.4 | 98.5 | 84.4 | 98.4 |
| N3II108MA111G4_E10 | 42.6 | 98.7 | 64.1 | 98.5 | 75.6 | 98.7 | 86.2 | 98.5 |

TABLE 8

Specific activity and TOF (turnover frequency) values of purified R-HNL variants after production in a 5 l fermenter: the variants PaHNL5αL1Q, A111G (WO 2004/083424) and the R-HNL variants of the invention were used for the (R)-2-chloromandelonitrile substrate.

| | Specific activity [$\mu$mol * min$^{-1}$ * mg$^{-1}$] | TOF [s$^{-1}$] |
|---|---|---|
| A111G | 424.8 +/− 26.1 | 410.7 +/− 25.2 |
| I108MA111G | 870.1 +/− 32.1 | 841.2 +/− 31.1 |
| N3II108MA111G4_E10 | 926.2 +/− 48.7 | 895.4 +/− 47.1 |

EXAMPLE 11

Cultivation of *Pichia pastoris* Transformants in Shaker Flasks and Characterization of the Enzyme Variants with Regard to Conversion of Hydroxypivalaldehyde A sufficient amount of enzyme was prepared from the clones *Pichia pastoris* GS115 pHILDPaHNL5αL1Q (WO 2004/083424), *Pichia pastoris* GS115 pHILDPaHNL5αL1Q, V317G (WO 2004/083424) and *Pichia pastoris* GS115 pHILD2-PaHNL5αV317A (see example 2 and example 5) in 2 l shaker cultures for initial characterizations.

A) Cultivation of *Pichia pastoris* Transformants

In each case 135 ml of BM0,5G medium (0.2 M potassium phosphate, pH 6.0; 13.4 g/l yeast nitrogen base, 5 g/l glycerol; 0.4 mg/l biotin) in 2 l flasks with baffles were inoculated with a large single colony and incubated with shaking at 120 rpm and 28° C., 80% humidity. Expression via the AOX1 promoter was induced by adding 15 ml of BMM10 medium (0.2 M potassium phosphate, pH 6.0; 13.4 g/l yeast nitrogen base; 50 ml/l methanol; 0.4 mg/l biotin) after 60-70 hours. Further methanol additions of 1.5 ml per shaker flask (150 ml) were carried out after 10, 24 and 48 hours.

Approx. 72 hours after the first methanol induction, the cells were removed by centrifugation and the culture supernatant was used directly, or in diluted or concentrated form for measuring enzyme activity.

B) Characterization of PaHNL5 Variants

The culture supernatant from the shaker flasks was concentrated approx. 20-fold by means of ultrafiltration (10 kDa cutoff) using 20 ml Vivaspin PES centrifugation columns from Sartorius (Göttingen, D). Protein concentration was subsequently carried out using a Biorad (Hercules, Calif.) protein assay (Bradford). The standard used for producing a calibration line was native PaHNL from Sigma (M-6782 Lot 41H4016).

Samples containing approx. 3 µg of total protein were taken from the concentrated enzyme preparations and applied directly to a gel (protein gel NuPAGE 4-12% Bis Gel 1.0 mm×15 well; Invitrogen). Furthermore, samples containing approx. 1.5 µg of total protein were deglycosylated by endoglycosidase H (Cat. #P0702L, NEB) according to the protocol provided by NEB and then applied. The standard used was SeeBlue Plus2 Pre-Stained Standard from Invitrogen (Carlsbad, USA). FIG. 2 depicts SDS-PAGEs of the PaHNL5αL1Q (=WT), V317G and V317A muteins.

C) Synthesis of (R)-hydroxypivalaldehyde Cyanohydrin:

To compare the selectivities of the mutants of the invention for converting hydroxypivalaldehyde to the corresponding (R)-cyanohydrin, in each case 1 mg of the corresponding PaHNL was diluted with 3 M citrate-phosphate buffer (pH 2.4) to a final volume of 5 ml. The buffered solution was adjusted again to pH 2.4 by adding 50% (w/w) citric acid solution and mixed with 120 mg of briefly heated, liquid hydroxypivalaldehyde in 30 ml glass vials. The solution was cooled to 4° C., and 100 µl of liquid HCN were metered in using a syringe. The solution was stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 9 depicts the results for conversion (% conv) and enantiomeric excess (% ee) of the R-HNL variants of the invention after different points in time.

TABLE 9

Conversion and enantiomeric excess of PaHNL5αL1Q (=WT), PaHNL5αL1Q, V317G (for both, see WO 2004/083424) and PaHNL5αV317A with the substrate hydroxypivalaldehyde with regard to synthesis of the corresponding (R)-cyanohydrin

| | Reaction time | | | | | |
|---|---|---|---|---|---|---|
| | 2.5 h | | 5 h | | 20.5 h | |
| PaHNL variant | Conv (%) | ee (%) | Conv (%) | ee (%) | Conv (%) | ee (%) |
| Blank (no enzyme) | 6.7 | rac | 8.4 | rac | 37.8 | rac |
| WT | 14.9 | 22.2 | n.d. | n.d. | 64.9 | 22.2 |
| V317G | 15.1 | 21.8 | 24.4 | 25.9 | 53.5 | 10.6 |
| V317A | 42.4 | 87.1 | 59.2 | 86.7 | 86.5 | 81.8 |

(n.d.—not determined; rac—racemic)

While the V317G variant achieved approximately the same enantiomeric excess and conversion in converting hydroxypivalaldehyde as the wild type (PaHNL5αL1Q), the V317A variant was able to achieve substantially better selectivities and conversions.

EXAMPLE 12

Production of the V317A Mutant in a 5 l Fermenter

A sufficient amount of enzyme was prepared from the clone *Pichia pastoris* GS115 pHILD2-PaHNL5αV317A (see example 2 and example 5) in a 5 l fermenter for further characterizations. A Mut$^s$ strain was chosen for culturing.

Firstly, a preculture comprising 50 ml of YPD medium (10 g/l Bacto™ yeast extract, 20 g/l Bacto™ peptone, 20 g/l D-glucose) was inoculated with a large single colony and incubated at 28° C. and 120 rpm for 24 h. Said first preculture was used for inoculating 2×200 ml of YPD medium in 2 l flasks with baffles. This was followed by approx. 10 h of incubation at 28° C. and 120 rpm.

All chemicals required for fermentation have been mentioned previously in example 9.

Chemicals 1-7, amounts calculated for 3.5 liters, were dissolved in deionized water and introduced into a 5 l bioreactor (Biostat® CT from Sartorius). After in situ sterilization, the pH of the medium was adjusted to pH 5.0 with 25% ammonia by way of sterile addition through a feed pump. This was followed by introducing into the bioreactor 13.5 ml of sterile-filtered trace element solution comprising vitamin H by means of a sterile syringe.

Approx. 400 ml of preculture from two 2 l shaker flasks were used for inoculation. The starting $OD_{600}$ in the fermenter was 1.2. With an operating temperature of 28° C., an aeration rate of 2.5-10 liters of air/min and a stirring speed between 500 and 1500 rpm, the partial pressure of oxygen ($pO_2$) was maintained at a value>30% of the saturation concentration. The pH of the culture medium was kept constant at pH 5.0 by sterile addition of 25% ammonia through a feed pump.

After the initially introduced glycerol had been consumed, after a fermentation time of 15-20 hours, metering-in of the glycerol medium was started, initially at 45 ml/h. The metering-in rate was increased in steps to 90-100 ml/h and continued for approx. 15 hours, until approx. 180 $OD_{600}$ were reached. Metering-in of glycerol was then stopped.

The third phase of fermentation was initiated by inducing expression by metering in methanol. The metering-in rate was adjusted initially to 10-15 ml/h. This rate was increased in steps to 45-60 ml/h over 12-15 hours and maintained for another 60 hours.

After approx. 72 hours of methanol induction, the cells were harvested by two centrifugations at 4000 rpm in a Beckman Coulter™ (Fullerton, Calif., USA) Avanti™ J-20XP centrifuge with the Beckman JLA 8.1000 rotor at 4° C. for 20 min. The culture supernatant was collected and the enzyme activity of (rac)-mandelonitrile cleavage was determined. The fermentation supernatant was diluted appropriately with 1 M phosphate-citrate buffer (pH 5.0) and, after addition of the mandelonitrile substrate solution (40 µl (rac)-mandelonitrile+5 ml 0.1 M phosphate-citrate buffer (pH 3.0)), the absorbance profile at 280 nm was monitored for 5 min. The enzyme activity in the culture supernatant after centrifugation was 62.4 U/ml, resulting in an enzyme yield of approx. 174 700 U, with a total yield of approx. 2.8 l of culture supernatant.

The culture supernatant was concentrated by means of crossflow ultrafiltration using 30 kDa cutoff modules from Sartorius (VIVASCIENCE Vivaflow 50 from Sartorius, Göttingen, D). In this way a V317A enzyme preparation with a protein concentration of 3.715 mg/ml and an enzyme activity of 316.1 U/ml (standard HNL assay with rac-mandelonitrile) was prepared. The enzyme preparation was divided into 1 ml or 6 ml aliquots and stored at −20° C. Since *Pichia pastoris* secretes hardly any of its own proteins into the culture supernatant, the enzyme produced and concentrated in this way was already very pure (see also FIG. 4).

Samples were taken at various points in time during fermentation. The cells were removed by centrifugation and the protein concentration of the culture supernatants was determined by means of Biorad (Hercules, Calif.) protein assay (Bradford). The standard used for preparing a calibration line was native PaHNL from Sigma (M-6782 Lot 41H4016).

Of the individual culture supernatants, 5 µl were applied directly to a gel (protein gel: NuPAGE 4-12% Bis Gel 1.0 mm×15 well; Invitrogen). Furthermore, in each case 3 µl of the culture supernatants were deglycosylated by endoglycosidase H (Cat. #P0702L, NEB) according to the protocol provided by the supplier, and subsequently applied. The standard used was SeeBlue Plus2 Pre-Stained Standard from Invitrogen (Carlsbad, USA). Protein gels with native and deglycosylated V317A samples at various points in time of the 5 l fermentation are depicted in FIGS. 3 and 4, respectively.

The enzyme preparations produced in the fermenter and then concentrated are purified chromatographically in a manner similar to example 10.

EXAMPLE 13

Monomerization of Hydroxypivalaldehyde

The compound hydroxypivalaldehyde is a dimer at room temperature:

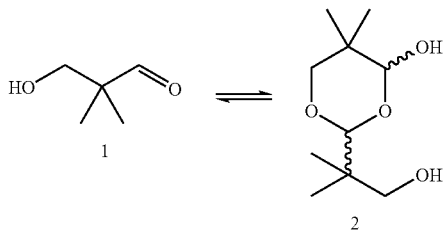

Equilibrium between hydroxypivalaldehyde monomer (1) and dimer (2)

For the reaction with HCN, the dimer was monomerized in order to obtain an exposed aldehyde group. The monomerization was carried out in two ways:

A) Thermal Monomerization:

For thermal monomerization, the hydroxypivalaldehyde dimer was heated in undiluted form at approx. 100° C. A secondary product was found to form in the process. The longer the aldehyde was heated at temperatures of approx. 100° C., the larger was the amount of secondary product formed. This product was produced by the "anomalous Tishchenko reaction" (Finch, J Org Chem, 1960, 25, 2219): 2,2-dimethyl-1,3-propanediol and 3-hydroxy-2,2-dimethylpropionic acid—compounds produced in a Cannizzaro reaction—fused to give 3-hydroxy-2,2-dimethylpropyl-3-hydroxy-2,2-dimethylpropionic ester (FIG. 6). All normal Tishchenko reactions (Tishchenko, J Russ Phys Chem Soc, 1906, 38:355, 482, 540, 547) require a Lewis acid and demand the absence of water (Fouquet et al., Liebigs Ann Chem, 1979, 10, 1591). In the present case, non-anhydrous conditions were used, and temperatures of approx. 100° C. were sufficient in order to form the fusion product by means of "anomalous Tishchenko reaction" (Finch, J Org Chem, 1960, 25, 2219). The mixture derivatized with acetic anhydride in the presence of pyridine and dichloromethane was analyzed by means of GC (FIG. 5) on a cyclodextrin column (CP-Chirasil-Dex CB). It was possible to fractionate the monomer, dimer and the produced ester:

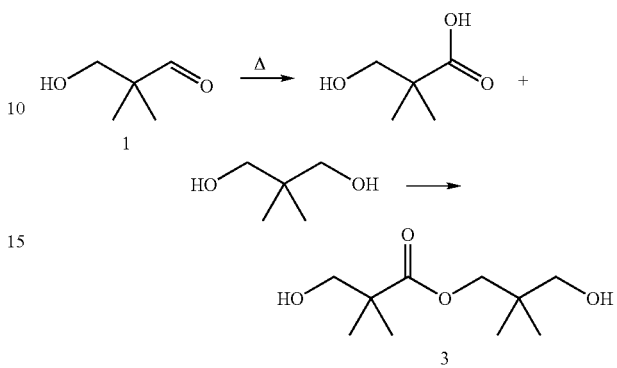

"Anomalous Tishchenko reaction" (Finch, J Org Chem, 1960, 25, 2219) with hydroxypivalaldehyde (1) to give 3-hydroxy-2,2-dimethylpropyl-3-hydroxy-2,2-dimethylpropionic ester (3)

B) Acid-Catalyzed Monomerization:

Acid-catalyzed hemiacetal cleavage of the dimer is also possible in order to shift the equilibrium to the monomer's side. Due to good stability of the PaHNL5 variants in acidic medium (WO 2004/083424), it was subsequently also possible to carry out enzyme-catalyzed addition of HCN at low pH values.

In order to test the properties of hydroxypivalaldehyde monomerization at different pH values, in each case 180 mg of liquid hydroxypivalaldehyde were admixed with 5 ml of 30 mM potassium phosphate buffer (pH 2.0-7.0) in 30 ml glass vials and stirred at 250 rpm and room temperature on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

The results are depicted in FIG. 8 and table 10. Monomerization of the hydroxypivalaldehyde dimer was shown to progress very slowly. Comparing the proportions of monomer after 28 h, the amount of hydroxypivalaldehyde monomer increased with decreasing pH of the solution (see table 10). After approx. 4 h (see FIG. 6), a relatively large proportion of monomer is also observed at higher pH values. However, at these pH values stereoselectivity of HCN addition in the presence of R-HNL is only low.

TABLE 10

Proportion of the hydroxypivalaldehyde monomer in buffered, aqueous solutions at different pH values after 28 h

| pH | Proportion of monomer (%) |
|---|---|
| 2.0 | 91 |
| 2.5 | 89 |
| 3.0 | 88 |
| 3.4 | 81 |
| 4.0 | 77 |
| 4.5 | 74 |
| 5.0 | 67 |
| 5.5 | 61 |
| 6.0 | 67 |
| 7.0 | 60 |

EXAMPLE 14

Characterization of the V317A Mutant Produced in a 5 l Fermenter, Using the Substrates Hydroxypivalaldehyde and Pivalaldehyde The influence of numerous reaction parameters on selectivity and activity of the V317A mutant was assayed. The V317A enzyme preparation from the 5 l fermentation was used in aqueous medium, in a two-phase system with MTBE and in immobilized form on Celite in an organic system. In the experiments below, one unit corresponds to the amount of enzyme that converts 1 μmol of mandelonitrile to benzaldehyde and HCN at pH 5.0 and room temperature in one minute.

A) Conversion of Hydroxypivalaldehyde in 2 M Potassium Phosphate Buffer at Different pH Values:

Reaction mixtures of 5 ml each were chosen for hydroxypivalaldehyde conversion at different pH values. 170 units of the concentrated V317A enzyme preparation (85.1 U/mg) were diluted with 2 M potassium phosphate buffer in 30 ml glass vials to give a final volume of 5 ml. For the corresponding blank reactions, the enzyme preparation was replaced with the same volume of deionized water. Reaction mixtures at pH 1.0, pH 1.5, pH 2.0, pH 2.5, pH 3.0, pH 4.0, pH 5.0, pH 6.0, pH 7.0 and pH 8.0 were carried out. After addition of the enzyme preparation or deionized water, the buffered solutions were again adjusted to the corresponding pH. This was followed by addition of 120 mg of briefly heated, liquid hydroxypivalaldehyde. The reaction mixtures were cooled at 4° C., and 100 μl (=2.2 equivalents) of liquid HCN were metered in using a syringe. The solution was stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 11 and FIG. 7 depict the results of conversion (% conv) and enantiomeric excess (% ee) at various points in time.

TABLE 11

Conversion and enantiomeric excess of V317A with hydroxypivalaldehyde at different pH values in 2 M potassium phosphate buffer (pH 1.0-8.0) (rac = racemic)

|  |  | 2 h | | 6 h | | 22 h | |
|---|---|---|---|---|---|---|---|
| pH |  | % ee | % conv | % ee | % conv | % ee | % conv |
| pH 1.0 | V317A | rac | 2.5 | rac | 3.9 | 15.7 | 3.5 |
|  | blank | rac | 2.6 | rac | 3.8 | 7.6 | 3.9 |
| pH 1.5 | V317A | 2.0 | 3.6 | 2.5 | 4.6 | 4.3 | 4.4 |
|  | blank | rac | 4.4 | rac | 6.0 | rac | 9.9 |
| pH 2.0 | V317A | 93.4 | 60.2 | 95.2 | 89.3 | 95.7 | 98.1 |
|  | blank | rac | 5.6 | 2.3 | 10.3 | 2.3 | 22.7 |
| pH 2.5 | V317A | 94.4 | 77.0 | 95.5 | 96.2 | 94.9 | 99.1 |
|  | blank | rac | 6.9 | 3.4 | 14.3 | rac | 38.2 |
| pH 3.0 | V317A | 93.8 | 73.2 | 95.0 | 95.6 | 94.3 | 99.2 |
|  | blank | rac | 12.3 | rac | 23.4 | rac | 66.5 |
| pH 4.0 | V317A | 66.7 | 50.9 | 70.7 | 62.0 | 71.3 | 82.4 |
|  | blank | rac | 42.9 | rac | 54.5 | 2.2 | 87.4 |
| pH 5.0 | V317A | 15.0 | 73.0 | 14.6 | 90.9 | 14.5 | 100 |
|  | blank | rac | 73.5 | rac | 88.8 | rac | 100 |
| pH 6.0 | V317A | 6.5 | 95.3 | 4.4 | 100 | 4.7 | 100 |
|  | blank | rac | 97.3 | rac | 100 | rac | 100 |
| pH 7.0 | V317A | rac | 99.9 | rac | 100 | rac | 100 |
|  | blank | rac | 99.9 | rac | 100 | rac | 100 |
| pH 8.0 | V317A | rac | 99.9 | rac | 100 | rac | 100 |
|  | blank | rac | 99.9 | rac | 100 | rac | 100 |

B) Conversion of Hydroxypivalaldehyde in 1 M Potassium Phosphate Buffer at Different pH Values:

Reaction mixtures of 5 ml each were chosen for hydroxypivalaldehyde conversion at different pH values. 170 units of the concentrated V317A enzyme preparation (85.1 U/mg) were diluted with 1 M potassium phosphate buffer in 30 ml glass vials to give a final volume of 5 ml. For the corresponding blank reactions, the enzyme preparation was replaced with the same volume of deionized water. Reaction mixtures at pH 1.5, pH 2.0, pH 2.5, pH 3.0, pH 4.0, pH 5.0 and pH 6.0 were carried out. After addition of the enzyme preparation or deionized water, the buffered solutions were again adjusted to the corresponding pH. This was followed by addition of 120 mg of briefly heated, liquid hydroxypivalaldehyde. The reaction mixtures were cooled at 4° C., and 100 μl (=2.2 equivalents) of liquid HCN were metered in using a syringe. The solution was stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 12 and FIG. 8 depict the results of conversion (% conv) and enantiomeric excess (% ee) at various points in time.

TABLE 12

Conversion and enantiomeric excess of V317A with hydroxypivalaldehyde at different pH values in 1M potassium phosphate buffer (V = V317A, B = blank, rac = racemic)

| | | pH 1.5 | | pH 2.0 | | pH 2.5 | | pH 3.0 | | pH 4.0 | | pH 5.0 | | pH 6.0 | |
|---|---|---|---|---|---|---|---|---|---|---|---|---|---|---|---|
| Time | | V | B | V | B | V | B | V | B | V | B | V | B | V | B |
| 2 h | % ee | 22.8 | rac | 93.5 | 1.3 | 93.8 | rac | 93.0 | 10.3 | 76.4 | 1.7 | 23.2 | 1.1 | 5.2 | rac |
|  | % conv | 1.8 | 2.0 | 42.9 | 3.5 | 73.3 | 6.5 | 52.3 | 11.5 | 34.2 | 30.5 | 48.1 | 47.2 | 89.8 | 91.9 |
| 6 h | % ee | 20.8 | rac | 95.2 | rac | 94.4 | rac | 93.9 | 1.3 | 74.1 | rac | 22.7 | rac | 4.1 | rac |
|  | % conv | 4.1 | 3.6 | 79.8 | 7.7 | 97.6 | 12.2 | 83.0 | 30.9 | 48.6 | 46.3 | 68.9 | 68.8 | 98.8 | 100 |
| 20 h | % ee | 15.0 | rac | 94.9 | rac | 94.6 | rac | 94.2 | 1.4 | 74.3 | rac | 22.1 | rac | 3.9 | rac |
|  | % conv | 5.8 | 6.0 | 98.3 | 15.4 | 100 | 36.1 | 98.0 | 70.2 | 73.1 | 73.0 | 93.2 | 93.9 | 100 | 100 |

The results of the conversions at different pH values revealed that a pH range from pH 2.0-3.0 is optimally suited to converting hydroxypivalaldehyde to the corresponding (R)-cyanohydrin. While the V317A enzyme does not have sufficient activity below pH 2.0, conversions at above pH 3.0 were adversely affected by the unselective chemical background reaction. This was indicated by decreasing enantiomeric excesses in the enzymatic reactions and by increasing conversions of the purely chemical reactions (blank reactions) with increasing pH.

C) Comparison of Different Buffer Concentrations:

The potassium phosphate buffer concentrations were varied further. 170 units of the concentrated V317A enzyme preparation (85.1 U/mg) were diluted with 50 mM, 100 mM, 1 M or 2 M potassium phosphate buffer (pH 2.5) in 30 ml glass vials to a final volume of 5 ml. In the blank reaction mixture, the enzyme preparation was replaced with the same volume of deionized water and a buffer concentration of 2 mol/l was chosen. The buffered solutions were adjusted again to pH 2.5 after addition of the enzyme preparation or the deionized water. This was followed by addition of 120 mg of briefly heated, liquid hydroxypivalaldehyde. The reaction mixtures were cooled at 4° C., and 100 µl (=2.2 equivalents) of liquid HCN were metered in using a syringe. The solutions were stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 13 depicts the results for conversion (% conv) and enantiomeric excess (% ee) at various points in time.

TABLE 13

Conversion and enantiomeric excess of V317A in an aqueous system with different potassium phosphate buffer concentrations (rac = racemic):

| | | Buffer concentration | | | | |
|---|---|---|---|---|---|---|
| Time | | 50 mM V317A | 100 mM V317A | 1M V317A | 2M V317A | 2M Blank |
| 2 h | % ee | 93.7 | 93.0 | 94.2 | 94.4 | rac |
| | % conv | 41.2 | 41.3 | 68.3 | 77.0 | 6.9 |
| 6 h | % ee | 94.9 | 94.5 | 95.0 | 95.5 | 3.4 |
| | % conv | 69.2 | 70.7 | 94.8 | 96.2 | 14.3 |
| 22 h | % ee | 95.5 | 94.5 | 95.3 | 94.9 | rac |
| | % conv | 98.7 | 98.8 | 99.4 | 99.1 | 38.2 |

When comparing conversion after 2 hours, a distinct difference was identified. The lower the buffer concentration, the lower the resulting conversion values. The enantiomeric excess remained roughly constant. With increasing reaction time, said difference disappeared almost completely. With a buffer concentration of 2 mol/l, 99.1% conversion was achieved after 22 h, while 98.7% conversion was measured with a buffer concentration of 50 mmol/l. The improved conversion with higher buffer concentrations can be explained by the fact that monomerization of the hydroxypivalaldehyde substrate proceeds faster with higher buffer concentrations, thereby providing a larger proportion of monomer for addition of HCN.

D) Variation in the Amount of Enzyme Used:

Three different amounts of enzyme were compared: 56 units, 112 units or 316 units of the concentrated V317A enzyme preparation were diluted with 3 M citrate-phosphate buffer (pH 2.5) in 30 ml glass vials to a final volume of 5 ml. In the blank reaction, the enzyme preparation was replaced with the same volume of deionized water. The buffered solutions were adjusted again to pH 2.5 after addition of the enzyme preparation or the deionized water. This was followed by addition of 120 mg of briefly heated, liquid hydroxypivalaldehyde. The reaction mixtures were cooled at 4° C., and 100 µl (=2.2 equivalents) of liquid HCN were metered in using a syringe. The solutions were stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 15 depicts the results for conversion (% conv) and enantiomeric excess (% ee) at various points in time.

TABLE 14

Conversion and enantiomeric excess of V317A in an aqueous system - variation in the amount of enzyme used (rac—racemic)

| Reaction time | | Blank | 56 Units | 112 Units | 316 Units |
|---|---|---|---|---|---|
| 2 h | % ee | rac | 87.6 | 92.5 | 94.5 |
| | % conv | 6.7 | 38.8 | 54.0 | 79.6 |
| 5 h | % ee | rac | 88.1 | 91.7 | 94.5 |
| | % conv | 8.4 | 56.2 | 74.8 | 93.3 |
| 20.5 h | % ee | rac | 81.7 | 89.4 | 94.5 |
| | % conv | 37.8 | 84.3 | 94.3 | 99.7 |

Hydroxypivalaldehyde was converted directly to the corresponding (R)-cyanohydrin with >94% enantiomeric excess and >93% conversion even within 5 h. An increase in the amount of enzyme resulted in improved enantiomeric excesses and conversions.

E) Variation in the Amount of Hydroxypivalaldehyde Used:

170 units of the concentrated V317A enzyme preparation were diluted with 2 M potassium phosphate buffer (pH 2.5) in 30 ml glass vials to a final volume of 5 ml. The buffered solutions were adjusted to pH 2.5 after addition of the enzyme preparation. This was followed by adding 13 mg, 56 mg or 120 mg liquid hydroxypivalaldehyde, corresponding to final concentrations of 25 mM, 110 mM and 235 mM hydroxypivalaldehyde, respectively. The reaction mixtures were cooled at 4° C., and 100 µl of liquid HCN were metered in using a syringe. The solutions were stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 15 depicts the results for conversion (% conv) and enantiomeric excess (% ee) at various points in time.

TABLE 15

Conversion and enantiomeric excess of V317A in an aqueous system - variation in the amount of substrate used

| Reaction time | | 120 mg HPA | 56 mg HPA | 13 mg HPA |
|---|---|---|---|---|
| 2 h | % ee | 94.4 | 94.5 | 95.5 |
| | % conv | 77.0 | 87.9 | 99.8 |
| 6 h | % ee | 95.5 | 95.0 | 97.0 |
| | % conv | 96.2 | 100 | 100 |
| 22 h | % ee | 94.9 | 94.9 | 97.5 |
| | % conv | 99.1 | 100 | 100 |

Conversion and enantiomeric excess were improved further by reducing the initial amount of hydroxypivalaldehyde. With an initial amount of hydroxypivalaldehyde of 13 mg, 97.0% ee and 100% conversion were achieved after 6 h. 97.5% enantiomeric excess and 100% conversion were achieved after 22 h.

F) Variation in the Amount of HCN Used:

170 units of the concentrated V317A enzyme preparation were diluted with 1 M potassium phosphate buffer (pH 2.5) in 30 ml glass vials to a final volume of 5 ml. In the blank reaction mixture, the enzyme preparation was replaced with the same volume of deionized water. The buffered solutions were adjusted to pH 2.5 after addition of the enzyme preparation or the deionized water. This was followed by addition of 120 mg of briefly heated, liquid hydroxypivalaldehyde. The reaction mixtures were cooled at 4° C., and 70 μl (1.5 equivalents), 90 μl (2.0 equivalents), 110 μl (2.5 equivalents), 140 μl (3.0 equivalents), 160 μl (3.5 equivalents) or 180 μl (4.0 equivalents) of liquid HCN were metered in using a syringe. The solutions were stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 16 depicts the results for conversion (% conv) and enantiomeric excess (% ee) at various points in time.

For the reaction mixtures with a purely aqueous system, 2 mg of the concentrated V317A enzyme preparation (=170 units) or 2 mg of PaHNL5 (WO 2004/083424) (=852 units) were diluted with 50 mM phosphate buffer (pH 3.4 and pH 5.1, respectively) in 30 ml glass vials to a final volume of 5 ml. After addition of the enzyme preparation, the buffered solutions were again adjusted to pH 3.4 and pH 5.1, respectively. This was followed by addition of 180 mg of briefly heated, liquid hydroxypivalaldehyde. The reaction mixtures were cooled at 4° C., and 100 μl of liquid HCN were metered in using a syringe. The solutions were stirred at 600 rpm on a Variomag Electronicrührer Poly 15 magnetic stirrer from H+P Labortechnik (Oberschleißheim, D).

For the reaction mixtures with two-phase system, 2 mg of the concentrated V317A enzyme preparation (=170 units) or 2 mg of PaHNL5 (WO 2004/083424) (=852 units) were diluted with 50 mM phosphate buffer (pH 3.4 and pH 5.1, respectively) in 30 ml glass vials to a final volume of 2.5 ml. After addition of the enzyme preparation, the buffered solutions were again adjusted to pH 3.4 and pH 5.1, respectively. This was followed by addition of 2.5 ml of methyl tert-butyl ether (MTBE) and 180 mg of briefly heated, liquid hydroxypivalaldehyde. The reaction mixtures were cooled at 4° C., and 100 μl of liquid HCN were metered in using a syringe.

TABLE 16

Conversion and enantiomeric excess of V317A in an aqueous system - variation in the amount of HCN used
(eq = equivalent, B = blank, V = V317A, rac = racemic)

| Reaction time | | 1.5 eq HCN | | 2.0 eq HCN | | 2.5 eq HCN | | 3.0 eq HCN | | 3.5 eq HCN | | 4.0 eq HCN | |
|---|---|---|---|---|---|---|---|---|---|---|---|---|---|
| | | V | B | V | B | V | B | V | B | V | B | V | B |
| 2 h | % ee | 94.6 | 3.9 | 95.5 | 3.9 | 94.4 | 2.1 | 94.3 | 2.0 | 94.5 | 2.7 | 94.0 | 3.1 |
| | % conv | 70.8 | 6.5 | 76.8 | 8.0 | 78.5 | 7.0 | 73.6 | 8.3 | 81.6 | 9.1 | 81.0 | 9.9 |
| 6 h | % ee | 95.8 | 1.8 | 95.9 | 2.9 | 95.1 | rac | 95.5 | rac | 94.7 | 1.8 | 94.8 | 1.5 |
| | % conv | 93.8 | 10.0 | 95.5 | 13.4 | 98.1 | 13.1 | 97.5 | 15.9 | 98.1 | 18.1 | 98.1 | 18.5 |
| 22 h | % ee | 95.9 | 1.2 | 95.6 | 1.9 | 95.6 | rac | 95.5 | rac | 94.9 | 1.6 | 94.4 | 1.3 |
| | % conv | 98.3 | 25.8 | 99.3 | 35.1 | 99.3 | 33.1 | 99.4 | 43.7 | 99.9 | 52.2 | 100 | 54.5 |

The results with different HCN amounts revealed only slight differences in enantiomeric excess. The increase in conversion with progressing reaction time was more clearly visible. Except conversion with 3.0 equivalents of HCN, it was possible to correlate a slight improvement in conversion with an initial elevated amount of HCN. Furthermore, a slight decrease in enantiomeric excess with an initial elevated amount of HCN was observed.

G) Conversion of Hydroxypivalaldehyde in the Two-Phase System and Comparison with a Purely Aqueous Solvent System:

The solutions were stirred at 600 rpm on a Variomag Electronicrührer Poly 15 magnetic stirrer from H+P Labortechnik (Oberschleißheim, D).

Samples were taken at various points in time, derivatized with acetic anhydride in the presence of pyridine and dichloromethane and analyzed by means of GC on a cyclodextrin column (CP-Chirasil-Dex CB).

Table 17 depicts the results for conversion (% conv) and enantiomeric excess (% ee) at various points in time.

TABLE 17

Conversion and enantiomeric excess of V317A and PaHNL5 (=WT) -
comparison of a purely aqueous system with a two-phase system at
2 different pH values

| | | Reaction system | | | | | | | |
|---|---|---|---|---|---|---|---|---|---|
| | | $H_2O$ | | | | $H_2O$/MTBE | | | |
| | | pH | | | | | | | |
| | | pH 3.4 | | pH 5.1 | | pH 3.4 | | pH 5.1 | |
| | Time | WT | V317A | WT | V317A | WT | V317A | WT | V317A |
| 4 h | % ee | 54.3 | 86.6 | 6.8 | 25 | 19.5 | 60.8 | 3.7 | 6.6 |
| | % conv | 26 | 31 | 37 | 38 | 12 | 16 | 28 | 27 |

TABLE 17-continued

Conversion and enantiomeric excess of V317A and PaHNL5 (=WT) - comparison of a purely aqueous system with a two-phase system at 2 different pH values

| | | Reaction system | | | | | | |
|---|---|---|---|---|---|---|---|---|
| | | H₂O | | | | H₂O/MTBE | | |
| | | pH | | | | | | |
| | | pH 3.4 | | pH 5.1 | | pH 3.4 | | pH 5.1 | |
| Time | | WT | V317A | WT | V317A | WT | V317A | WT | V317A |
| 24 h | % ee | 52.6 | 87.5 | 8.6 | 29.5 | 20.7 | 58.2 | 4.7 | 8.6 |
| | % conv | 47 | 54 | 58 | 56 | 30 | 29 | 35 | 32 |

The V317A mutant was shown to convert the hydroxypivalaldehyde substrate to the corresponding (R)-cyanohydrin more rapidly and with higher enantioselectivity than the PaHNL5 wild type, both in the purely aqueous solution and in the two-phase system (H₂O/MTBE). This again demonstrated that an increase in pH results in a reduction of enantiomeric excess. The results further indicate that a purely aqueous reaction system is to be preferred over a two-phase system (H₂O/MTBE) for conversion of hydroxypivalaldehyde. The two-phase system achieved smaller enantiomeric excesses and lower conversions.

H) Immobilization of V317A or PaHNL5 on Celite® and Conversion of Hydroxypivalaldehyde in the Microaqueous, Organic Solvent System 2 g of Celite® 545 were introduced to a 50 ml glass beaker and stirred with 20 ml of 50 mM phosphate buffer (pH 7.0) on a magnetic stirrer at room temperature for 45 min. The Celite® was then filtered off and washed thoroughly with deionized water. 50 ml round-bottomed flasks were charged in each case with 140 mg of washed Celite® to which 8.6 ml of 30 mM potassium phosphate buffer (pH 3.4) were added. Furthermore, 1.41 mg of the concentrated V317A enzyme preparation (=120 units) or 1.41 mg of PaHNL5 (WO 2004/083424) (=600 units) were added. The mixtures were mixed well and frozen in liquid N₂ on a Rotavapor (BÜCHI Labortechnik AG, Flawil, CH) and lyophilized at 0.040 mbar and −50° C. for 14 h 30 min.

The immobilized substances were transferred to 10 ml round-bottomed flasks and admixed with 2970 µl of diisopropyl ether (DIPE), 24.8 µl of 30 mM potassium phosphate buffer (pH 3.4) and 120 mg of briefly heated, liquid hydroxypivalaldehyde. The reaction mixtures were stirred at room temperature on a Heidolph Instruments (D) MR 3001 magnetic stirrer and started by adding 100 µl of liquid HCN.

Samples were taken at various points in time, derivatized with acetic anhydride in the presence of pyridine and dichloromethane and analyzed by means of GC on a cyclodextrin column (CP-Chirasil-Dex CB).

Table 18 depicts the results for conversion (% conv) and enantiomeric excess (% ee) at various points in time.

TABLE 18

Conversion and enantiomeric excess of V317A and PaHNL5 (=WT) immobilized on Celite ® in the microaqueous, organic solvent system (rac = racemic)

| Reaction time | | WT | V317A | Blank |
|---|---|---|---|---|
| 2 h | % ee | 95.5 | 94.0 | rac |
| | % conv | 23 | 22 | 0 |
| 6 h | % ee | 96.1 | 95.5 | rac |
| | % conv | 26 | 26 | 0 |
| 20 h | % ee | 97.2 | 96.9 | 2.8 |
| | % conv | 36 | 37 | 3 |

When immobilized on Celite® in the microaqueous, organic solvent system, both the V317A mutant and the PaHNL5 wild type showed comparable enantioselectivities. After 20 hours, an enantiomeric excess of approx. 97% was achieved. However, a disadvantage of this reaction system is the slow monomerization of the hydroxypivalaldehyde dimer in the organic solvent, DIPE, and the moderate conversions resulting therefrom.

I) Preparative Conversion of 1.2 q of Hydroxypivalaldehyde with V317A Mutein in a 100 ml Reactor In a 100 ml Schmizo reactor with KPG stirrer (Schmizo AG, Zofingen, CH), 3 mg of the concentrated V317A enzyme preparation (=255 units) were diluted with 2 M potassium phosphate buffer (pH 2.5) to a final volume of 50 ml. The pH was checked and adjusted again to pH 2.5. This was followed by adding 1.2 g of briefly heated, liquid hydroxypivalaldehyde (final concentration: 235 mM). Thus only 0.255 mg of enzyme per mmol of hydroxypivalaldehyde was used. The reaction mixture was cooled at 4° C. and stirred vigorously. Finally, the reaction was started by adding 1 ml of liquid HCN.

Workup commenced after a reaction time of 20 h. The reaction solution was discharged from the reactor and extracted three times with methyl tert-butyl ether (MTBE). The organic phases were combined, dried over Na₂SO₄ and concentrated on a rotary evaporator.

After derivatization with acetic anhydride in the presence of pyridine and dichloromethane, analysis was carried out by means of GC on a cyclodextrin column (CP-Chirasil-DEX CB).

The yield of the reaction after 20 h was 88% with 96% ee.

J) Conversion of Pivalaldehyde to (R)-2-hydroxy-3,3-dimethylbutyronitrile with V317A or PaHNL5

2 mg of the concentrated V317A enzyme preparation (=170 units) or 2 mg of PaHNL5 (WO 2004/083424) (=852 units) were diluted with 30 mM phosphate buffer (pH 3.4) in 30 ml glass vials to a final volume of 5 ml. After addition of the enzyme preparation, the buffered solutions were again adjusted to pH 3.4. This was followed by addition of 200 µl of pivalaldehyde. The reaction mixtures were cooled at 4° C. and stirred at 600 rpm for 10 min. Then 100 µl of liquid HCN were metered in using a syringe. The solutions were stirred on a Variomag Electronicrührer Poly 15 magnetic stirrer from H+P Labortechnik (Oberschleißheim, D) at 600 rpm during the reaction.

Samples were taken at various points in time, derivatized with acetic anhydride in the presence of pyridine and dichloromethane and analyzed by means of GC on a cyclodextrin column (CP-Chirasil-Dex CB).

Table 19 depicts the results for conversion (% conv) and enantiomeric excess (% ee) at various points in time.

TABLE 19

Conversion and enantiomeric excess of V317A and PaHNL5 (=WT) with pivalaldehyde

| Reaction time | | WT | V317A |
|---|---|---|---|
| 2 h | % ee | 76.8 | 95.7 |
| | % conv | 98 | 100 |
| 4 h | % ee | 76.9 | 95.1 |
| | % conv | 100 | 100 |

With the V317A mutein, quantitative conversion with 95.7% ee was found even after a reaction time of 2 h.

EXAMPLE 15

Conversion of Pivalaldehyde to (R)-2-hydroxy-3,3-dimethylbutyronitrile with V317A and PaHNL5

A sufficient amount of enzyme was prepared from the clones *Pichia pastoris* GS115 pHILD2-PaHNL5αV317A or *Pichia pastoris* GS115 pHILD2-PaHNL5 (WO 2004/083424) in 5 l bioreactors for further characterizations. The culture supernatant was concentrated in each case approx. 6-fold by means of Crossflow Ultrafiltration using 30 kDa cutoff modules from Sartorius (VIVASCIENCE Vivaflow 50 from Sartorius, Göttingen, D).

In 30 ml glass vials, 2 mg, 3 mg or 4 mg of the concentrated V317A enzyme preparation (=170 units, 256 units and 341 units, respectively) or 2 mg, 3 mg or 4 mg of the concentrated PaHNL5 enzyme preparation (=545 units, 817 units and 1089 units, respectively) were diluted with 1 M phosphate buffer (pH 3.0) to a final volume of 5 ml. The buffered solutions were again adjusted to pH 3.0 after addition of the enzyme preparation. This was followed by addition of 200 μl of pivalaldehyde (Sigma-Aldrich, T71501). The reaction mixtures were cooled at 9° C. 100 μl of liquid HCN were metered in using a syringe. The solutions were stirred on a Variomag Electronicrührer Poly 15 magnetic stirrer from H+P Labortechnik (Oberschleißheim, D) at 600 rpm during the reaction.

Samples were taken at various points in time, derivatized with acetic anhydride in the presence of pyridine and dichloromethane and analyzed by means of GC on a cyclodextrin column (CP-Chirasil-Dex CB).

Table 1 depicts the results for conversion (% conv) and enantiomeric excess (% ee) at various points in time.

TABLE 1

Conversion and enantiomeric excess of V317A and PaHNL5 (=WT) with pivalaldehyde

| Reaction time | | Blank | WT 2 mg | WT 3 mg | WT 4 mg | V317A 2 mg | V317A 3 mg | V317A 4 mg |
|---|---|---|---|---|---|---|---|---|
| 1 h | % ee | rac | 82.5 | 87.5 | 90.4 | 97.3 | 97.5 | 97.4 |
| | % conv | 33.8 | 77.8 | 82.8 | 89.6 | 99.9 | 99.8 | 99.9 |
| 2 h | % ee | rac | 85.0 | 89.4 | 91.7 | 97.2 | 97.4 | 97.4 |
| | % conv | 46.7 | 94.2 | 96.6 | 99.7 | 100 | 100 | 100 |
| 6 h | % ee | rac | 86.3 | 89.9 | 91.9 | 97.2 | 97.4 | 97.4 |
| 10 min | % conv | 72.8 | 100 | 100 | 100 | 100 | 100 | 100 |

With the V317A mutein, quantitative conversion with 97.5% ee was found even after a reaction time of 1 h.

We claim:

1. A synthetic R-hydroxynitrile lyase comprising an amino acid sequence which is a variant of SEQ ID NO: 29, wherein the variant differs from SEQ ID NO: 29 solely by (i) amino acid substitution of alanine with glycine at a position corresponding to position 111 of SEQ ID NO: 29 and (ii) amino acid substitution of one or more positions corresponding to positions selected from 3, 108, 110, 304, 85, 209, 278, 432, 424, 225, 1, and 317 of SEQ ID NO: 29, and wherein if position 110 is substituted then the amino acid substitution is substitution of asparagine with serine, if position 225 is substituted then the amino acid substitution is substitution of asparagine with serine, if position 1 is substituted then the amino acid substitution is substitution of leucine with glutamine, and if position 317 is substituted then the amino acid substitution is substitution of valine with alanine.

2. The synthetic R-hydroxynitrile lyase of claim 1, wherein the synthetic R-hydroxynitrile lyase is obtained by introducing the amino acid substitutions in an R-hydroxynitrile lyase isolated from the group consisting of *Prunus amygdalus* (PaHNL), *Prunus serotina* (PsHNL), *Prunus avium, Prunus laurocerasus, Prunus lyonii, Prunus armaniaca, Prunus persica, Prunus domestica* (PdHNL), *Prunus mume* (PmHNL), *Malus communis, Malus pumila,* and *Cydonia oblonga*.

3. The synthetic R-hydroxynitrile lyase of claim 1, wherein the synthetic R-hydroxynitrile lyase comprises a signal sequence selected from the group consisting of signal sequences of the alpha mating factor of *Saccharomyces cerevisiae, Saccharomyces cerevisiae* invertase, the *Pichia* killer toxin, α-amylase, *Pichia pastoris* acid phosphatase, *Phaseolus vulgaris* agglutinin, the *Aspergillus niger* glucoamylase, the *Aspergillus niger* glucose oxidase, the *Pichia pastoris* Sec10 signal sequence, the 28 kD subunit of the *Kluyveromyces lactis* killer toxin, and the signal sequence of BSA.

4. The synthetic R-hydroxynitrile lyase of claim 1, wherein the amino acid substitutions are introduced by random mutagenesis, defective polymerase reactions, sequence saturation mutagenesis, complete active site saturation assay, site-specific mutagenesis, gene site saturation mutagenesis, chemical mutagenesis, mutator strains or physical methods.

5. The synthetic R-hydroxynitrile lyase of claim 1, wherein the synthetic R-hydroxynitrile lyase is encoded by a nucleotide sequence obtained by DNA shuffling or by combining mutations of a first mutated nucleic acid and a second mutated nucleic acid.

6. The synthetic R-hydroxynitrile lyase of claim 1, wherein the synthetic R-hydroxynitrile lyase has been screened by high throughput screening or high throughput selection methods, using a suitable nitrile, a suitable aldehyde or a suitable ketone as substrate, with either cleavage of the nitrile being monitored or conversion of the corresponding aldehyde or ketone to the corresponding cyanohydrins being analyzed.

7. The synthetic R-hydroxynitrile lyase of claim 1, wherein the amino acid residue corresponding to position 108 of SEQ ID NO: 29 is replaced with methionine and/or the amino acid residue corresponding to position 3 of SEQ ID NO: 29 is replaced with isoleucine.

8. The synthetic R-hydroxynitrile lyase of claim 1, wherein the amino acid substitution of one or more positions is/are selected from the group consisting of:
 a) replacement of isoleucine on position 304 by valine,
 b) replacement of isoleucine on position 108 by methionine,
 c) replacement of asparagine on position 110 by serine,
 d) replacement of asparagine on position 3 by isoleucine,
 e) replacement of isoleucine on position 108 by methionine in combination with replacement of tyrosine on position 432 by phenylalanine in combination with replacement of valine on position 424 by alanine,
 f) replacement of asparagine on position 3 by isoleucine in combination with replacement of isoleucine on position 108 by methionine,
 g) replacement of isoleucine on position 108 by methionine in combination with replacement of asparagine on position 110 by serine,
 h) replacement of isoleucine on position 108 by methionine in combination with replacement of asparagine on position 225 by serine,
 i) replacement of isoleucine on position 108 by methionine in combination with replacement of valine on position 317 by alanine, and
 j) replacement of valine on position 317 by alanine.

9. A process for preparing enantiomerically pure cyanohydrins comprising reacting an aliphatic, aromatic or heteroaromatic aldehyde or ketone with the synthetic R-hydroxynitrile lyase of claim 1 in the presence of a cyanide group donor at a temperature of from −10° C. to +50° C. and at a pH of 1.8 to pH 7.0 to form a corresponding cyanohydrin.

10. The synthetic R-hydroxynitrile lyase of claim 1, comprising a signal sequence having the amino acid sequence from amino acid 1 to amino acid 27 of SEQ ID NO: 28.

11. The synthetic R-hydroxynitrile lyase of claim 7, wherein the nucleotide tri let coding for the amino acid at a position corresponding to position 85 of SEQ ID NO: 29 is CCG and the nucleotide triplet coding for the amino acid at a position corresponding to position 432 of SEQ ID NO: 29 is TAC.

12. The synthetic R-hydroxynitrile lyase of claim 1, wherein the nucleotide triplet coding for the amino acid at a position corresponding to position 85 of SEQ ID NO: 29 is CCG and the nucleotide triplet coding for the amino acid at a position corresponding to position 432 of SEQ ID NO: 29 is TAC.

13. The synthetic R-hydroxynitrile lyase of claim 1, wherein the amino acid substitution of one or more positions is substitution of isoleucine on position 108 with methionine.

14. The synthetic R-hydroxynitrile lyase of claim 1, wherein the amino acid substitution of one or more positions is substitution of asparagine on position 3 with isoleucine in combination with substitution of isoleucine on position 108 with methionine.

15. The synthetic R-hydroxynitrile lyase of claim 1, wherein the amino acid substitution of one or more positions is substitution of isoleucine on position 108 with methionine in combination with substitution of asparagine on position 225 with serine.

16. The synthetic R-hydroxynitrile lyase of claim 1, wherein the amino acid substitution of one or more positions is substitution of isoleucine on position 108 with methionine in combination with substitution of valine on position 317 with alanine.

17. The synthetic R-hydroxynitrile lyase of claim 1, wherein the amino acid substitution of one or more positions is substitution of valine on position 317 with alanine.

18. The process of claim 9, wherein the reaction is carried out in an organic system, aqueous system, 2-phase system, or emulsion.

* * * * *

UNITED STATES PATENT AND TRADEMARK OFFICE
CERTIFICATE OF CORRECTION

PATENT NO.        : 8,846,366 B2                              Page 1 of 1
APPLICATION NO.   : 12/519095
DATED             : September 30, 2014
INVENTOR(S)       : Richard Gaisberger et al.

It is certified that error appears in the above-identified patent and that said Letters Patent is hereby corrected as shown below:

In The Claims

Claim 11, column 60, line 24, "wherein the nucleotide tri let coding for the amino acid at a" should read:

-- wherein the nucleotide triplet coding for the amino acid at a --

Signed and Sealed this
Tenth Day of March, 2015

Michelle K. Lee
*Deputy Director of the United States Patent and Trademark Office*

SEQUENCE LISTING

<160> NUMBER OF SEQ ID NOS: 29

<210> SEQ ID NO 1
<211> LENGTH: 39
<212> TYPE: DNA
<213> ORGANISM: Artificial Sequence
<220> FEATURE:
<223> OTHER INFORMATION: primer HNL5alpha1lq

<400> SEQUENCE: 1
agagaggctg aagctcaagc caatacttct gctcatgat        39

<210> SEQ ID NO 2
<211> LENGTH: 36
<212> TYPE: DNA
<213> ORGANISM: Artificial Sequence
<220> FEATURE:
<223> OTHER INFORMATION: primer HNL5alpha21aq

<400> SEQUENCE: 2
gaagtattgg cttgagcttc agcctctctt ttctcg           36

<210> SEQ ID NO 3

```
<211> LENGTH: 26
<212> TYPE: DNA
<213> ORGANISM: Artificial Sequence
<220> FEATURE:
<223> OTHER INFORMATION: primer Ocyctermrv1

<400> SEQUENCE: 3
tgctcacatg ttggtctcca gcttgc                                          26

<210> SEQ ID NO 4
<211> LENGTH: 47
<212> TYPE: DNA
<213> ORGANISM: Artificial Sequence
<220> FEATURE:
<223> OTHER INFORMATION: primer PaHNL4L1Qendf3

<400> SEQUENCE: 4
gtcagatagc gaggtcactc agtccgaaca aaaactcatc tcagaag                   47

<210> SEQ ID NO 5
<211> LENGTH: 42
<212> TYPE: DNA
<213> ORGANISM: Artificial Sequence
<220> FEATURE:
<223> OTHER INFORMATION: primer PaHNL5endBr

<400> SEQUENCE: 5
gactgagtga cctcgctatc tgactcacat ggactcttga at                        42

<210> SEQ ID NO 6
<211> LENGTH: 19
<212> TYPE: DNA
<213> ORGANISM: Artificial Sequence
<220> FEATURE:
<223> OTHER INFORMATION: primer pGAP158for

<400> SEQUENCE: 6
ccttctctct ccttccacc                                                  19

<210> SEQ ID NO 7
<211> LENGTH: 25
<212> TYPE: DNA
<213> ORGANISM: Artificial Sequence
<220> FEATURE:
<223> OTHER INFORMATION: primer pGAPZA484f

<400> SEQUENCE: 7
ttcgaaacga ggaattcacg atgag                                           25

<210> SEQ ID NO 8
<211> LENGTH: 25
<212> TYPE: DNA
<213> ORGANISM: Artificial Sequence
<220> FEATURE:
<223> OTHER INFORMATION: primer pGAPZA484r

<400> SEQUENCE: 8
ctcatcgtga attcctcgtt tcgaa                                           25

<210> SEQ ID NO 9
<211> LENGTH: 52
<212> TYPE: DNA
<213> ORGANISM: Artificial Sequence
<220> FEATURE:
<223> OTHER INFORMATION: primer A111Mutfor
<220> FEATURE:
<221> NAME/KEY: misc_feature
```

<222> LOCATION: (25)..(26)
<223> OTHER INFORMATION: "n" is equal to a, t, c, or g
<220> FEATURE:
<221> NAME/KEY: misc_feature
<222> LOCATION: (31)..(32)
<223> OTHER INFORMATION: "n" is equal to a, t, c, or g

<400> SEQUENCE: 9
atcctcggtg gcacgaccat aatcnnkgga nnkgtctacg ccagagctaa ca        52

<210> SEQ ID NO 10
<211> LENGTH: 25
<212> TYPE: DNA
<213> ORGANISM: Artificial Sequence
<220> FEATURE:
<223> OTHER INFORMATION: primer A111rev

<400> SEQUENCE: 10
gattatggtc gtgccaccga ggatc        25

<210> SEQ ID NO 11
<211> LENGTH: 24
<212> TYPE: DNA
<213> ORGANISM: Artificial Sequence
<220> FEATURE:
<223> OTHER INFORMATION: primer V113Xshortfwd

<400> SEQUENCE: 11
tacgccagag ctaacatttc attc        24

<210> SEQ ID NO 12
<211> LENGTH: 51
<212> TYPE: DNA
<213> ORGANISM: Artificial Sequence
<220> FEATURE:
<223> OTHER INFORMATION: primer V113Xlongrev
<220> FEATURE:
<221> NAME/KEY: misc_feature
<222> LOCATION: (26)..(27)
<223> OTHER INFORMATION: "n" is equal to a, t, g or c

<400> SEQUENCE: 12
gaatgaaatg ttagctctgg cgtamnngcc tgcattgatt atggtcgtgc c        51

<210> SEQ ID NO 13
<211> LENGTH: 62
<212> TYPE: DNA
<213> ORGANISM: Artificial Sequence
<220> FEATURE:
<223> OTHER INFORMATION: primer V317Xlongfwd
<220> FEATURE:
<221> NAME/KEY: misc_feature
<222> LOCATION: (26)..(27)
<223> OTHER INFORMATION: "n" is equal to a, t, g, or c

<400> SEQUENCE: 13
cccaaatcca attgaagcct ctgttnnkac tgttttaggc attagaagtg attattatca        60
ag        62

<210> SEQ ID NO 14
<211> LENGTH: 24
<212> TYPE: DNA
<213> ORGANISM: Artificial Sequence
<220> FEATURE:
<223> OTHER INFORMATION: primer V317Xshortrev

<400> SEQUENCE: 14
aacagaggct tcaattggat ttgg                                              24

<210> SEQ ID NO 15
<211> LENGTH: 59
<212> TYPE: DNA
<213> ORGANISM: Artificial Sequence
<220> FEATURE:
<223> OTHER INFORMATION: primer V329Xlongfwd
<220> FEATURE:
<221> NAME/KEY: misc_feature
<222> LOCATION: (33)..(34)
<223> OTHER INFORMATION: "n" is equal to a, t, g, or c

<400> SEQUENCE: 15
ctgttttagg cattagaagt gattattatc aannktctct gtcaagcttg ccattttcc       59

<210> SEQ ID NO 16
<211> LENGTH: 32
<212> TYPE: DNA
<213> ORGANISM: Artificial Sequence
<220> FEATURE:
<223> OTHER INFORMATION: primer V329Xshortrev

<400> SEQUENCE: 16
ttgataataa tcacttctaa tgcctaaaac ag                                     32

<210> SEQ ID NO 17
<211> LENGTH: 49
<212> TYPE: DNA
<213> ORGANISM: Artificial Sequence
<220> FEATURE:
<223> OTHER INFORMATION: primer V329Xlongfwd
<220> FEATURE:
<221> NAME/KEY: misc_feature
<222> LOCATION: (25)..(26)
<223> OTHER INFORMATION: "n" is equal to a, t, g or c

<400> SEQUENCE: 17
ccaaattcga cttttgctca tattnnkagc caagttccag gaccattgt                   49

<210> SEQ ID NO 18
<211> LENGTH: 24
<212> TYPE: DNA
<213> ORGANISM: Artificial Sequence
<220> FEATURE:
<223> OTHER INFORMATION: primer V360Xshortrev

<400> SEQUENCE: 18
aatatgagca aaagtcgaat ttgg                                              24

<210> SEQ ID NO 19
<211> LENGTH: 43
<212> TYPE: DNA
<213> ORGANISM: Artificial Sequence
<220> FEATURE:
<223> OTHER INFORMATION: primer HNL5alp21

<400> SEQUENCE: 19
atggtaccga attctcacat ggactcttga atattatgaa tag                         43

<210> SEQ ID NO 20
<211> LENGTH: 33
<212> TYPE: DNA
<213> ORGANISM: Artificial Sequence
<220> FEATURE:
<223> OTHER INFORMATION: primer N31f

<400> SEQUENCE: 20

```
gctgaagctc aagccattac ttctgctcat gat                                33
```

<210> SEQ ID NO 21
<211> LENGTH: 33
<212> TYPE: DNA
<213> ORGANISM: Artificial Sequence
<220> FEATURE:
<223> OTHER INFORMATION: primer N3Ir

<400> SEQUENCE: 21

```
atcatgagca gaagtaatgg cttgagcttc agc                                33
```

<210> SEQ ID NO 22
<211> LENGTH: 33
<212> TYPE: DNA
<213> ORGANISM: Artificial Sequence
<220> FEATURE:
<223> OTHER INFORMATION: primer I108Mf

<400> SEQUENCE: 22

```
ctcggtggca cgaccatgat cagtggaggc gtc                                33
```

<210> SEQ ID NO 23
<211> LENGTH: 33
<212> TYPE: DNA
<213> ORGANISM: Artificial Sequence
<220> FEATURE:
<223> OTHER INFORMATION: primer I108Mr

<400> SEQUENCE: 23

```
gacgcctcca ctgatcatgg tcgtgccacc gag                                33
```

<210> SEQ ID NO 24
<211> LENGTH: 33
<212> TYPE: DNA
<213> ORGANISM: Artificial Sequence
<220> FEATURE:
<223> OTHER INFORMATION: primer I108M2f

<400> SEQUENCE: 24

```
ctcggtggca cgaccatgat caatggaggc gtc                                33
```

<210> SEQ ID NO 25
<211> LENGTH: 33
<212> TYPE: DNA
<213> ORGANISM: Artificial Sequence
<220> FEATURE:
<223> OTHER INFORMATION: primer I108M2r

<400> SEQUENCE: 25

```
gacgcctcca ttgatcatgg tcgtgccacc gag                                33
```

<210> SEQ ID NO 26
<211> LENGTH: 44
<212> TYPE: DNA
<213> ORGANISM: Artificial Sequence
<220> FEATURE:
<223> OTHER INFORMATION: primer N225Sf

<400> SEQUENCE: 26

```
gaagatcctc ttctcttcct ctacatcaaa tttgtcagct attg                    44
```

<210> SEQ ID NO 27
<211> LENGTH: 44
<212> TYPE: DNA

<213> ORGANISM: Artificial Sequence
<220> FEATURE:
<223> OTHER INFORMATION: primer N225Sr

<400> SEQUENCE: 27
caatagctga caaatttgat gtagaggaag agaagaggat cttc                           44

<210> SEQ ID NO 28
<211> LENGTH: 559
<212> TYPE: PRT
<213> ORGANISM: Prunus amygdalus

<400> SEQUENCE: 28

```
Met Glu Lys Ser Thr Met Ser Val Ile Leu Phe Val Leu His Leu Leu
1               5                   10                  15

Val Leu His Leu Gln Tyr Ser Glu Val His Ser Leu Ala Asn Thr Ser
                20                  25                  30

Ala His Asp Phe Ser Tyr Leu Lys Phe Val Tyr Asn Ala Thr Asp Thr
            35                  40                  45

Ser Ser Glu Gly Ser Tyr Asp Tyr Ile Val Ile Gly Gly Gly Thr Ser
        50                  55                  60

Gly Cys Pro Leu Ala Ala Thr Leu Ser Glu Lys Tyr Lys Val Leu Leu
65                  70                  75                  80

Leu Glu Arg Gly Thr Ile Ala Thr Glu Tyr Pro Asn Thr Leu Thr Ala
                85                  90                  95

Asp Gly Phe Ala Tyr Asn Leu Gln Gln Gln Asp Asp Gly Lys Thr Pro
            100                 105                 110

Val Glu Arg Phe Val Ser Glu Asp Gly Ile Asp Asn Val Arg Ala Arg
        115                 120                 125

Ile Leu Gly Gly Thr Thr Ile Ile Asn Ala Gly Val Tyr Ala Arg Ala
130                 135                 140

Asn Ile Ser Phe Tyr Ser Gln Thr Gly Ile Glu Trp Asp Leu Asp Leu
145                 150                 155                 160

Val Asn Lys Thr Tyr Glu Trp Val Glu Asp Ala Ile Val Val Lys Pro
                165                 170                 175

Asn Asn Gln Ser Trp Gln Ser Val Ile Gly Glu Gly Phe Leu Glu Ala
            180                 185                 190

Gly Ile Leu Pro Asp Asn Gly Phe Ser Leu Asp His Glu Ala Gly Thr
        195                 200                 205

Arg Leu Thr Gly Ser Thr Phe Asp Asn Asn Gly Thr Arg His Ala Ala
210                 215                 220

Asp Glu Leu Leu Asn Lys Gly Asp Pro Asn Asn Leu Leu Val Ala Val
225                 230                 235                 240

Gln Ala Ser Val Glu Lys Ile Leu Phe Ser Ser Asn Thr Ser Asn Leu
                245                 250                 255

Ser Ala Ile Gly Val Ile Tyr Thr Asp Ser Asp Gly Asn Ser His Gln
            260                 265                 270

Ala Phe Val Arg Gly Asn Gly Glu Val Ile Val Ser Ala Gly Thr Ile
        275                 280                 285

Gly Thr Pro Gln Leu Leu Leu Leu Ser Gly Val Gly Pro Glu Ser Tyr
290                 295                 300

Leu Ser Ser Leu Asn Ile Thr Val Val Gln Pro Asn Pro Tyr Val Gly
305                 310                 315                 320

Gln Phe Val Tyr Asp Asn Pro Arg Asn Phe Ile Asn Ile Leu Pro Pro
                325                 330                 335
```

```
Asn Pro Ile Glu Ala Ser Val Val Thr Val Leu Gly Ile Arg Ser Asp
            340                 345                 350

Tyr Tyr Gln Val Ser Leu Ser Ser Leu Pro Phe Ser Thr Pro Pro Phe
        355                 360                 365

Ser Leu Phe Pro Thr Thr Ser Tyr Pro Leu Pro Asn Ser Thr Phe Ala
370                 375                 380

His Ile Val Ser Gln Val Pro Gly Pro Leu Ser His Gly Ser Val Thr
385                 390                 395                 400

Leu Asn Ser Ser Ser Asp Val Arg Ile Ala Pro Asn Ile Lys Phe Asn
                405                 410                 415

Tyr Tyr Ser Asn Ser Thr Asp Leu Ala Asn Cys Val Ser Gly Met Lys
        420                 425                 430

Lys Leu Gly Asp Leu Leu Arg Thr Lys Ala Leu Glu Pro Tyr Lys Ala
            435                 440                 445

Arg Asp Val Leu Gly Ile Asp Gly Phe Asn Tyr Leu Gly Val Pro Leu
        450                 455                 460

Pro Glu Asn Gln Thr Asp Asp Ala Ser Phe Glu Thr Phe Cys Leu Asp
465                 470                 475                 480

Asn Val Ala Ser Tyr Trp His Tyr His Gly Gly Ser Leu Val Gly Lys
                485                 490                 495

Val Leu Asp Asp Ser Phe Arg Val Met Gly Ile Lys Ala Leu Arg Val
            500                 505                 510

Val Asp Ala Ser Thr Phe Pro Tyr Glu Pro Asn Ser His Pro Gln Gly
        515                 520                 525

Phe Tyr Leu Met Leu Gly Arg Tyr Val Gly Leu Gln Ile Leu Gln Glu
530                 535                 540

Arg Ser Ile Arg Leu Glu Ala Ile His Asn Ile Gln Glu Ser Met
545                 550                 555

<210> SEQ ID NO 29
<211> LENGTH: 532
<212> TYPE: PRT
<213> ORGANISM: Prunus amygdalus

<400> SEQUENCE: 29

Leu Ala Asn Thr Ser Ala His Asp Phe Ser Tyr Leu Lys Phe Val Tyr
1               5                   10                  15

Asn Ala Thr Asp Thr Ser Ser Glu Gly Ser Tyr Asp Tyr Ile Val Ile
            20                  25                  30

Gly Gly Gly Thr Ser Gly Cys Pro Leu Ala Ala Thr Leu Ser Glu Lys
        35                  40                  45

Tyr Lys Val Leu Leu Leu Glu Arg Gly Thr Ile Ala Thr Glu Tyr Pro
50                  55                  60

Asn Thr Leu Thr Ala Asp Gly Phe Ala Tyr Asn Leu Gln Gln Gln Asp
65                  70                  75                  80

Asp Gly Lys Thr Pro Val Glu Arg Phe Val Ser Glu Asp Gly Ile Asp
                85                  90                  95

Asn Val Arg Ala Arg Ile Leu Gly Gly Thr Thr Ile Ile Asn Ala Gly
            100                 105                 110

Val Tyr Ala Arg Ala Asn Ile Ser Phe Tyr Ser Gln Thr Gly Ile Glu
        115                 120                 125

Trp Asp Leu Asp Leu Val Asn Lys Thr Tyr Glu Trp Val Glu Asp Ala
130                 135                 140

Ile Val Val Lys Pro Asn Asn Gln Ser Trp Gln Ser Val Ile Gly Glu
145                 150                 155                 160
```

```
Gly Phe Leu Glu Ala Gly Ile Leu Pro Asp Asn Gly Phe Ser Leu Asp
            165                 170                 175
His Glu Ala Gly Thr Arg Leu Thr Gly Ser Thr Phe Asp Asn Asn Gly
            180                 185                 190
Thr Arg His Ala Ala Asp Glu Leu Leu Asn Lys Gly Asp Pro Asn Asn
        195                 200                 205
Leu Leu Val Ala Val Gln Ala Ser Val Glu Lys Ile Leu Phe Ser Ser
    210                 215                 220
Asn Thr Ser Asn Leu Ser Ala Ile Gly Val Ile Tyr Thr Asp Ser Asp
225                 230                 235                 240
Gly Asn Ser His Gln Ala Phe Val Arg Gly Asn Gly Glu Val Ile Val
                245                 250                 255
Ser Ala Gly Thr Ile Gly Thr Pro Gln Leu Leu Leu Leu Ser Gly Val
                260                 265                 270
Gly Pro Glu Ser Tyr Leu Ser Ser Leu Asn Ile Thr Val Val Gln Pro
            275                 280                 285
Asn Pro Tyr Val Gly Gln Phe Val Tyr Asp Asn Pro Arg Asn Phe Ile
        290                 295                 300
Asn Ile Leu Pro Pro Asn Pro Ile Glu Ala Ser Val Val Thr Val Leu
305                 310                 315                 320
Gly Ile Arg Ser Asp Tyr Tyr Gln Val Ser Leu Ser Ser Leu Pro Phe
                325                 330                 335
Ser Thr Pro Pro Phe Ser Leu Phe Pro Thr Thr Ser Tyr Pro Leu Pro
                340                 345                 350
Asn Ser Thr Phe Ala His Ile Val Ser Gln Val Pro Gly Pro Leu Ser
            355                 360                 365
His Gly Ser Val Thr Leu Asn Ser Ser Ser Asp Val Arg Ile Ala Pro
    370                 375                 380
Asn Ile Lys Phe Asn Tyr Tyr Ser Asn Ser Thr Asp Leu Ala Asn Cys
385                 390                 395                 400
Val Ser Gly Met Lys Lys Leu Gly Asp Leu Leu Arg Thr Lys Ala Leu
                405                 410                 415
Glu Pro Tyr Lys Ala Arg Asp Val Leu Gly Ile Asp Gly Phe Asn Tyr
            420                 425                 430
Leu Gly Val Pro Leu Pro Glu Asn Gln Thr Asp Asp Ala Ser Phe Glu
        435                 440                 445
Thr Phe Cys Leu Asp Asn Val Ala Ser Tyr Trp His Tyr His Gly Gly
    450                 455                 460
Ser Leu Val Gly Lys Val Leu Asp Asp Ser Phe Arg Val Met Gly Ile
465                 470                 475                 480
Lys Ala Leu Arg Val Val Asp Ala Ser Thr Phe Pro Tyr Glu Pro Asn
                485                 490                 495
Ser His Pro Gln Gly Phe Tyr Leu Met Leu Gly Arg Tyr Val Gly Leu
            500                 505                 510
Gln Ile Leu Gln Glu Arg Ser Ile Arg Leu Glu Ala Ile His Asn Ile
        515                 520                 525
Gln Glu Ser Met
        530
```